US012579302B2

(12) United States Patent
Saavedra et al.

(10) Patent No.: US 12,579,302 B2
(45) Date of Patent: Mar. 17, 2026

(54) TOKEN AND PRIVACY DEVICE AND METHOD

(71) Applicant: LogicMark, Inc., Louisville, KY (US)

(72) Inventors: Rafael Saavedra, Sunnyvale, CA (US);
Chia-Lin Simmons, Moraga, CA (US);
Peter Williams, Belmont, CA (US)

(73) Assignee: LogicMark, Inc., Louisville, KY (US)

( * ) Notice: Subject to any disclaimer, the term of this
patent is extended or adjusted under 35
U.S.C. 154(b) by 199 days.

(21) Appl. No.: 18/221,820

(22) Filed: Jul. 13, 2023

(65) Prior Publication Data

US 2023/0385445 A1     Nov. 30, 2023

Related U.S. Application Data

(63) Continuation-in-part of application No. 18/197,590,
filed on May 15, 2023.

(60) Provisional application No. 63/365,457, filed on May
27, 2022.

(51) Int. Cl.
*G06F 21/02* (2006.01)
*G06F 21/62* (2013.01)
*G16H 40/67* (2018.01)

(52) U.S. Cl.
CPC ......... *G06F 21/6245* (2013.01); *G16H 40/67*
(2018.01)

(58) Field of Classification Search
CPC ...... H04L 9/3213; H04L 9/50; G06F 21/6245
See application file for complete search history.

(56) References Cited

U.S. PATENT DOCUMENTS

| | | | |
|---|---|---|---|
| 8,126,729 B2 | 2/2012 | Dicks et al. | |
| 8,966,235 B2* | 2/2015 | Dicks | G06F 8/61 |
| | | | 713/2 |
| 10,430,557 B2* | 10/2019 | Bowers | H04L 67/52 |
| 12,444,201 B2* | 10/2025 | Tusch | G06T 7/55 |
| 2015/0169314 A1* | 6/2015 | Dicks | G06F 8/61 |
| | | | 713/2 |
| 2017/0225447 A1* | 8/2017 | Varadan | B41F 17/00 |
| 2018/0027006 A1 | 1/2018 | Zimmermann et al. | |
| 2019/0320988 A1* | 10/2019 | Ahmed | A61B 5/002 |
| 2020/0090805 A1 | 3/2020 | Bowers et al. | |
| 2020/0227160 A1 | 7/2020 | Youngblood et al. | |
| 2020/0311304 A1 | 10/2020 | Parthasarathy | |
| 2021/0182422 A1* | 6/2021 | Basu | H04L 9/3213 |
| 2021/0202107 A1* | 7/2021 | Bostic | G16H 15/00 |
| 2022/0068501 A1 | 3/2022 | Gholami et al. | |
| 2022/0101710 A1* | 3/2022 | Tunnell | A61B 5/746 |
| 2023/0130656 A1 | 4/2023 | Park et al. | |
| 2023/0326589 A1* | 10/2023 | Saavedra | G16H 40/67 |
| | | | 705/2 |
| 2023/0385445 A1* | 11/2023 | Saavedra | G16H 40/67 |

OTHER PUBLICATIONS

PCT/US2023/022278, "International Preliminary Report on Patent-
ability", Dec. 12, 2024, 7 pages.

(Continued)

*Primary Examiner* — Dhairya A Patel
(74) *Attorney, Agent, or Firm* — K&L Gates LLP

(57) ABSTRACT

A system, apparatus, and method to monitor an event
associated with a person and report the event as a tokens to
other devices or to a central server.

20 Claims, 21 Drawing Sheets

(56)         References Cited

OTHER PUBLICATIONS

PCT/US2023/027672, "International Search Report and Written Opinion", Oct. 19, 2023, 9 pages.
PCT/US2023/022278, "International Search Report and the Written Opinion", Aug. 14, 2023, 9 pages.
WIPO; International Preliminary Report on Patentability for International Patent Application No. PCT/US2023/027672 dated Nov. 27, 2025, 8 pages.

* cited by examiner

TOKEN AND PRIVACY DEVICE AND METHOD

CROSS-REFERENCE TO RELATED APPLICATIONS

This application is continuation-in-part of U.S. patent application Ser. No. 18/197,590, filed on May 15, 2023, which claims priority to U.S. Provisional Patent Application No. 63/365,457, filed on May 27, 2022, and is incorporated by reference herein in its entirety.

BACKGROUND

Field of the Disclosure

The management and distribution of data from one person, including the devices and/or services that represent that person, to another and/or from a person to an organization is often based on an explicit or implicit agreement that is favorable to the recipient of the data. For example, many online services have terms of service that require the provider of the data to agree to uses of their data that suit the commercial objectives of the recipient.

There are many other situations where the recipient has processes, rules and their own regulations that require a provider to impart data that is not relevant to, or is tangential to, the interaction being undertaken.

This particularly important in the domain of health and health care, where the privacy of a person with a health care condition is of paramount importance and governed by law.

SUMMARY

Embodiments include a system and method to enhance the privacy of a data provider device in a manner that enables both provider and recipient to undertake the interactions required to achieve the outcomes both have agreed to without the provider compromising their privacy.

Aspects include a system, apparatus, and method to monitor an event associated with a person and to report the event as a tokens to other devices or to a central server.

The tokens may contain the sensor data or may reference the data stored at the sensor. Other devices in the system or the server may make decisions on event response or escalation, without the need to access the information stored or referenced by the tokens. Other devices within the system may obtain the data associated to the token and use it to, for example, enhance the event detection accuracy or to confirm the event. The device may interpret a combination of acceleration and change in altitude from its sensors as a "fall" event, issue a token associated with the sensors' data and send that event token to the server and to a nearby edge device. While the server may trigger a notification to a call center or to smart speaker app to initiate a conversation with the person, the nearby edge device may use the token, combined with its identification or other authorization key, to request the event data from the device and use it to confirm and/or add accuracy to the fall event, by combining the sensor data with data from its own sensors, for example audio signals from a microphone or microphone array, or output signals from one or more Frequency-Modulated Continuous-Wave (FMCW) radar sensors.

In one embodiment, a system protects privacy of a person under care by an at least one stakeholder. A plurality of environmental sensors monitor the person under care resulting in a detected data set. The environmental sensors provide a token comprising the detected data set representing behaviors of the person under care in an environment. The token is encrypted using an encryption key. Each of the behaviors is represented by a multi-dimensional feature set forming part of a health care profile (HCP) for the person under care. A care processing system comprises a transceiver, a token services module, a non-transitory computer-readable storage medium, and at least one hardware processing unit. The transceiver receives the token from the plurality of environmental sensors. The token services module decrypts the token using the encryption key. The non-transitory computer-readable storage medium stores a quiescent data set; the quiescent data set represents previous quiescent behaviors of the person under care in the environment. The at least one hardware processing unit determines a wellness or care event for the person under care by comparing the token and the quiescent data set. When the wellness or care event has occurred, the care processing system is configured to notify the at least one stakeholder.

In some embodiments, the encryption key is selected based in part on the detected data set, the at least one stakeholder, on the person under care, a type of event detected by the environmental sensor, or is unique to a session of the person under care.

In an alternate embodiment, a system protects privacy of a person under care by at least one stakeholder. A plurality of environmental sensors monitors the person under care resulting in a detected data set, and provides the detected data set representing behaviors of the person under care in an environment. Each of the behaviors is represented by a multi-dimensional feature set forming part of a health care profile for the person under care. A care processing system comprises a transceiver, a token services module, a non-transitory computer-readable storage medium, and at least one hardware processing unit. The transceiver receives the detected data set from the plurality of environmental sensors. The non-transitory computer-readable storage medium stores a quiescent data set. The quiescent data set representing previous quiescent behaviors of the person under care in the environment. The at least one hardware processing unit determines a wellness or care event for the person under care by comparing the token and the quiescent data set. When the wellness or care event has occurred, a token services module encrypts a token comprising the wellness or care event using an encryption key, and the care processing system notifies the at least one stakeholder.

In some embodiments, the encryption key is selected based in part on the detected data set, the at least one stakeholder, on the person under care, a type of event detected by the environmental sensor, or is unique to a session of the person under care.

In yet another embodiment, a system protects privacy of a person under care by an at least one stakeholder. A plurality of environmental sensors monitors the person under care resulting in a detected data set. The detected data set representing behaviors of the person under care in an environment; each of the behaviors is represented by a multi-dimensional feature set forming part of a health care profile for the person under care. The plurality of environmental sensors also stores the detected data set at the data repository, and provides a data token. The data token comprises a pointer to the detected data set at the data repository. The data token is encrypted using an encryption key. A care processing system comprises a transceiver, a token services module, a non-transitory computer-readable storage medium, and at least one hardware processing unit. The transceiver configured to receive the data token from the plurality of environmental sensors. The token services module decrypts the pointer from the data token using the encryption key. The transceiver receives the detected data set specified by the pointer from the data repository. The non-transitory computer-readable storage medium stores a quiescent data set. The quiescent data set represents previous quiescent behaviors of the person under care in the environment. The at least one hardware processing unit to determine a wellness or care event for the person under care by comparing the detected data set and the quiescent data set. When the wellness or care event has occurred, the care processing system is configured to notify the at least one stakeholder.

In some embodiments, the data repository stores the detected data set in a distributed ledger as a blockchain token. The distributed ledger may be a permissioned blockchain.

In some embodiments, the encryption key is selected based in part on: the detected data set, the at least one stakeholder, the person under care, a type of event detected by the environmental sensor, or a session of the person under care.

In yet another embodiment, a system protects privacy of a person under care by an at least one stakeholder. A plurality of environmental sensors monitor the person under care, and provide a detected data set representing behaviors of the person under care in an environment. Each of the behaviors is represented by a multi-dimensional feature set forming part of a health care profile for the person under care. The plurality of environmental sensors store the detected data set at the data repository, and provide a pointer to the detected data set at the data repository. A care processing system comprises a transceiver, a token services module, a non-transitory computer-readable storage medium, and at least one hardware processing unit. The transceiver receives the detected data set from the plurality of environmental sensors. The non-transitory computer-readable storage medium stores a quiescent data set. The quiescent data set represents previous quiescent behaviors of the person under care in the environment. The at least one hardware processing unit determines a wellness or care event for the person under care by comparing the token and the quiescent data set. When the wellness or care event has occurred, a token services module is configured to encrypt a data token comprising the detected data set or the wellness or care event using an encryption key, and the care processing system notifies the at least one stakeholder.

In some embodiments, the data repository stores the detected data set in a distributed ledger as a blockchain token. The distributed ledger may be a permissioned blockchain.

In some embodiments, the encryption key is selected based in part on: the detected data set, the at least one stakeholder, the person under care, a type of event detected by the environmental sensor, or a session of the person under care.

BRIEF DESCRIPTION OF THE DRAWINGS

These and other aspects will now be described in detail with reference to the following drawings.

DETAILED DESCRIPTION

Figure 1:
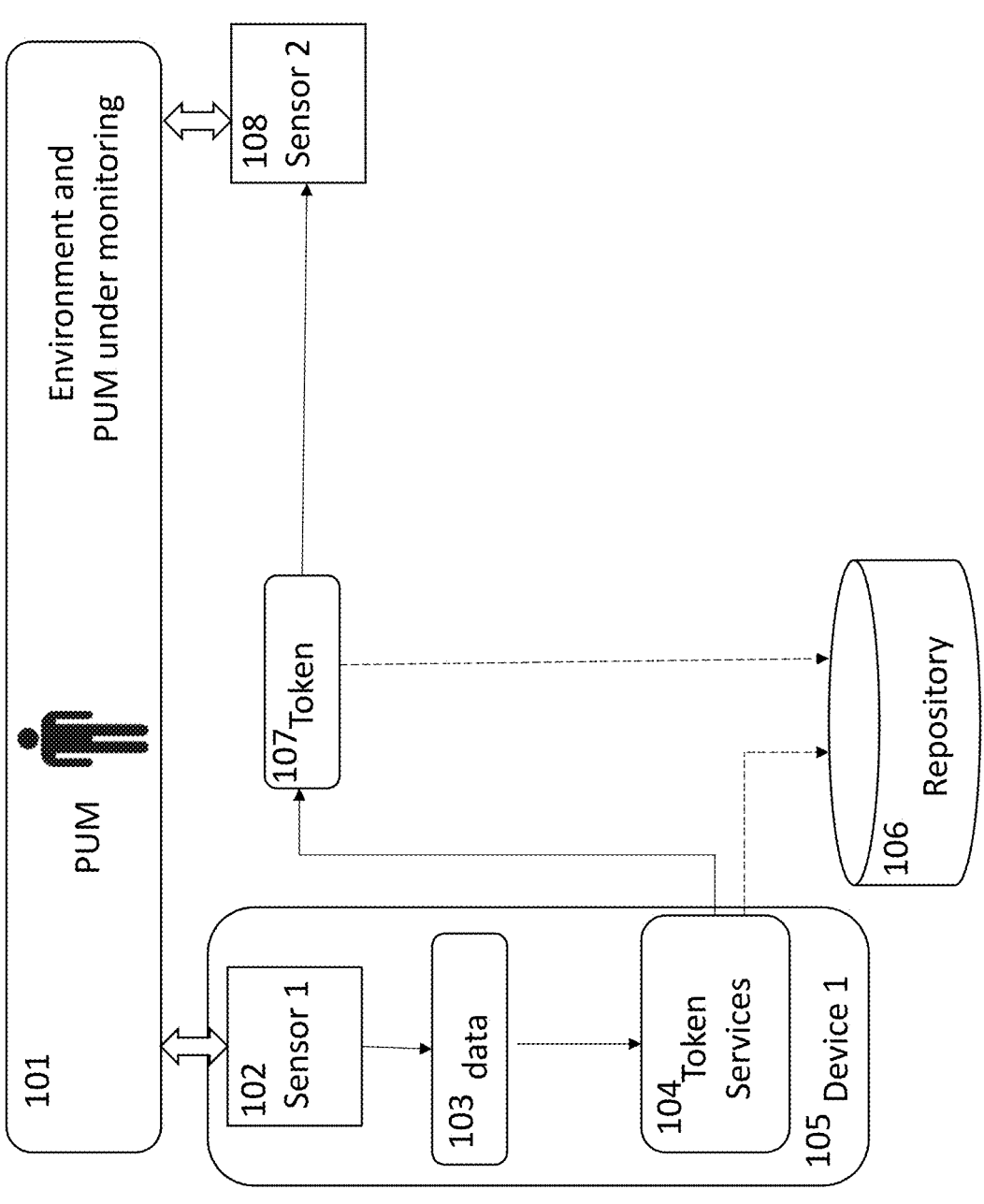
FIG. 1 illustrates an embodiment includes a sensor that generates data and includes a token services module that generates a token.

Aspects of the present disclosure include a system and method include an apparatus and method to enhance the privacy of a data provider device in a manner that enables both provider and recipient to undertake the interactions required to achieve the outcomes both have agreed to without the provider compromising their privacy.

A person may choose to disclose whatever information they feel appropriate to another party, however when that other party has a device that senses the activity, environment, communications and/or acts as a proxy for another person or organization, the choice of such information disclosure is, at least in part, often compromised.

In the case of a device, the degree to which the person has a trust relationship with that device can, at least in part, determine the degree of disclosure a person may make to that device. For example, in the case of access control and authorizations, the person may delegate to the device certain attributes, that enable that device to act as a proxy for that person, for example in the case of near field transactions. The device may also be used as a repository for certain data, such as passwords and other confidential data that the person wished to keep secure.

There are many examples of various trust relationships between a person and their device, such as their smart phone, vehicle, other smart devices and the like. However, as each of these devices and many others have sensing capabilities, there is a considerable amount of data that can be accumulated and can represent, directly or indirectly, the health condition of that person.

One approach to resolving the tension between the collection of such data, the use to which it may be put, and the persons desire for privacy and control of that data flow is the use of tokens to represent the data and any communications, storage, manipulation, management and/or other uses of that data.

There have been prior approaches to this situation using rules-based systems, where declarative rules are expressed and enforced in pursuit of the control, dissemination and management of the data, however the flexibility, efficiency, breadth and scope of such rule-based systems is ultimately limited to the use cases considered by their implementors.

This conundrum is exacerbated in the use of the Internet of Things (IoT) devices, where a plethora of devices having different capabilities, including inherent security, including a wide range of sensing capabilities makes the possibility of having an effective rules-based system impractical.

When these sensing capabilities are applied to a person with at least one health condition, there is a potential for a vast amount of data to be available to parties with access to those devices and/or sensors. The use of sensors, whether worn, carried or embedded in an environment is increasing substantially. The use of these sensors to provide data about a person, particularly related to their health is also increasing substantially.

There are many sensors that can be applied to an environment to determine activities in that environment. These include those that actively transmit a signal into the environment, those that capture photons or other electromagnetic frequencies from the environment, those that capture acoustic and other air pressure signals from the environment and those that are portable and carried into the environment. There are many devices that incorporate these sensors and others, such as accelerometers, gyroscopes, temperature, humidity, movement detectors, cameras, microphones and the like in various combinations.

A sensor can collect, measure, process, store and/or transmit data in any combination, depending on the capabilities of the sensor, the configuration and/or command and control systems of the sensor or connected to the sensor. In some embodiments, a sensor can measure, store and/or transmit data based on the capabilities and configuration of the sensor. A sensor can be collecting and/or measuring or not, as determined by the state of the sensor, which in turn is configured by a system. In the case where the sensor is measuring, it may be neither storing or transmitting any data. A sensor may measure, store and not transmit any data or may be configured to transmit data on demand, such as when triggered either by specifications held by the device or on receiving one or more commands from the system.

A key aspect of the system described herein is the use of tokens as a means for the communication, transfer and/or use of the data collected by t one or more sensor, where such data forms, at least in part, a system for monitoring the health condition of a person under monitoring (PUM).

The combination of PUM and other persons and/or organizations with whom they regularly interact, collectively stakeholders, the environment the PUM is usually domiciled in, as well other environments they may traverse, including the devices, services, stakeholders and other ephemera that they may interact with, together can form a care village.

Within this care village and for interactions with other entities external to the village, tokens may be used as the means of data exchange for any purpose.

Token Characteristics

A token can be any format, simply being a representation of a set of data. However most all instantiations of a token have a cryptographic formation such that the data the token represents is only available to authorized, authenticated persons and/or entities. For example, public key encryption creates tokens that require an encryption key (for example, a private key) to access the data represented therein. Tokens may be cryptographically signed and/or encrypted depending on the intended use of these tokens. The data sets represented by the tokens may range from simple integer/characters/algorithms to complex and/or organized sets of data that can form ontologies, hierarchies, taxonomies and/or other organizational data structures, which in turn may have at least one set of specifications governing, in whole or in part, their representation, communication, storage, disclosure and/or other characteristics.

FIG. 1 illustrates a device (105), which includes a sensor (102) that generates data (103) and includes a token services module (104) that generates a token (107), which in this example is communicated to a second sensor (108) and is stored in a repository (106), all whilst device 1 (105) and sensor 2 (108) are monitoring a PUM in their environment (101). In some embodiments, token services (104) may also record the generation of the token (107) in a repository, for example a distributed ledger.

Tokens may represent any data set by reference or embedding, including arrangements of other tokenized data. The use of tokens as representations of data can include the representation of stored data, where that data can be stored, for example, on or in a sensor, device and/or internal or external data repository. This can include cloud-based storage, where further access, authorization and authentication processing may be configured.

In some embodiments tokens may be recorded, in whole or in part, in one or more distributed ledger, to provide an immutable record. In this manner the token and/or the data the token represents is recorded and, for example, where that data represents a care or other event, establishes the occurrence of the event in a manner that supports an immutable audit trail, without disclosing the data. The only access to the data is available to those authorized to have such access, through for example the use of a public-encryption key pair.

For example, a stakeholder such as a care service, providing a caretaker to attend a PUM at their domicile, can know that the event of their attendance occurred, and potentially other data pertinent to that occurrence, without knowing specific details regarding the PUM condition that the PUM may wish to remain private.

This functionality can be configured though a token comprising a set of other tokenized data sets, where the access and authentication is such that only specific data is made available to the relevant stakeholder.

This combination of tokenized data arranged to enable multiple stakeholders' participation in multiple data sets, whilst maintaining the privacy of other stakeholders in the care village supports and enables the multiple care, commercial, insurance and/or other facilitated interactions.

Figure 2:
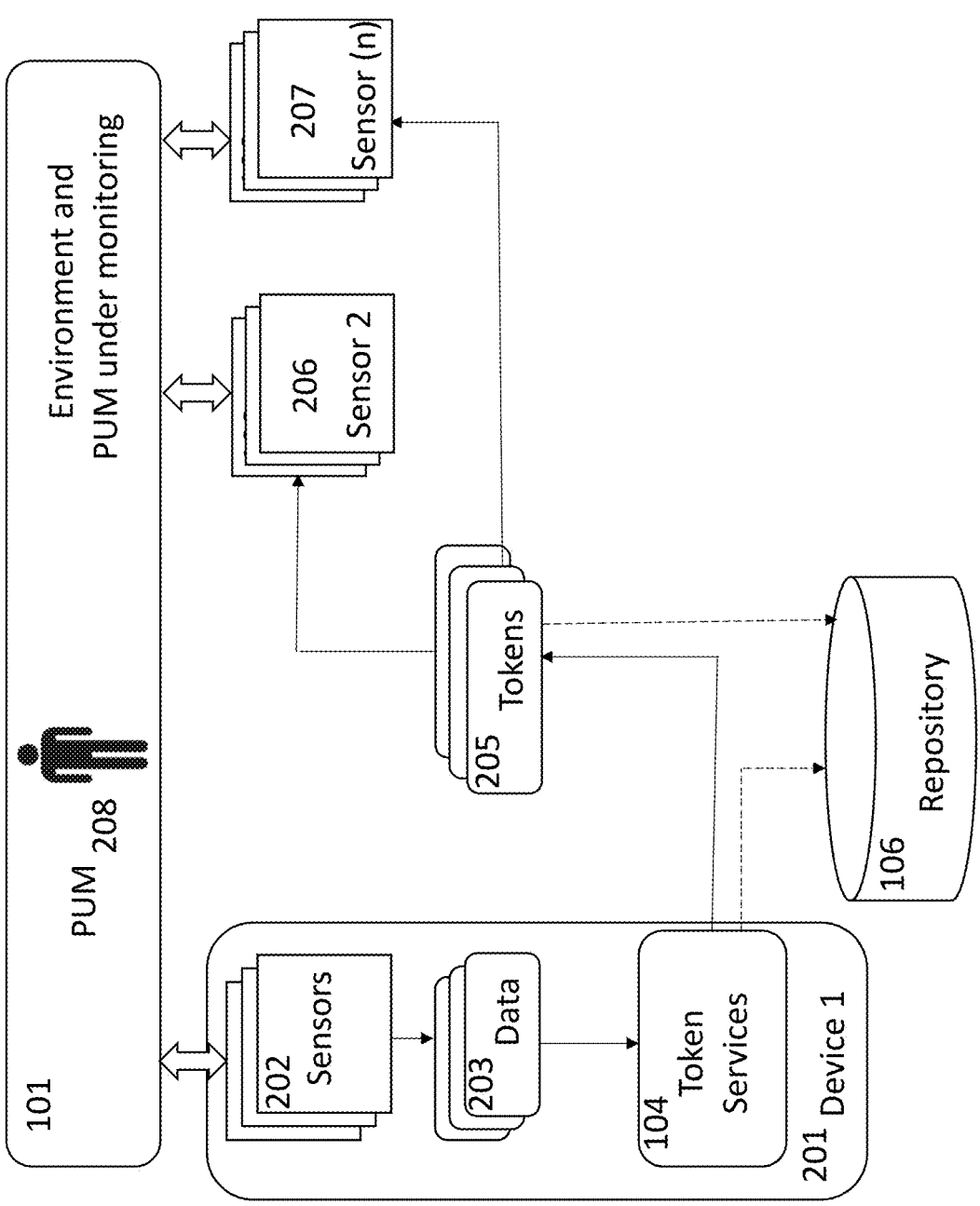
FIG. 2 illustrates an embodiment includes a set of sensors that generates data sets and includes a token services module that generates a set of tokens.

FIG. 2 illustrates a device (201), which includes a set of sensors (202) that generates data sets (203) and includes a token services module (104) that generates a set of tokens (205), which in this example is communicated to further sensors (206, 207) and can be stored in a repository (106), all whilst device 1 (105) and sensor 2 (206) and sensors (n) (207) are monitoring a PUM (208) in their environment (101). In some embodiments, token services (104) may also record the generation of the token (107) in a repository, for example a distributed ledger. In some embodiments sensors 2 (206) and sensors (n) (207) may be embedded in further devices and/or may incorporated directly into the environment under monitoring (101). This can include devices carried and/or worn by a PUM (208).

Token State

In some embodiments, tokens may have certain characteristics determining their state, such as for example, temporal, validity, transaction, value, verification and/or other attributes and/or characteristics, including conditions and/or other specifications. Each of these may be in the form of specifications, which can be embedded or referenced. These specifications can include access, authorization and/or authentication conditions, such that only in circumstances that match the specifications of the token, can the token data be available to another party, including for example, another token.

This capability may be used in situations where a set of sensors, for example within a specific domain, such as the environment of a PUM, exchange tokens between themselves, one or more care signal processing system and/or one or more digital twin, in any arrangement. These interactions may form a network for the care and wellness benefit of the PUM and yet the specifications of each token may restrict any other stakeholder, other than those that form the network, from accessing data for those tokens.

This network of tokens may also have state, in that such a network may be invoked by at least one environment sensing system, care signal processing system and/or authorized command and control system so as to aid in the care and wellness of a PUM. For example, if a PUM has a care event that requires immediate action, such as a fall, then the network may be invoked for the period of the response to that condition. After the situation has been resolved, such a network, potentially comprising sensors, devices, stakeholders, digital twins, care signal processing, predicative analytic systems and the like, may be returned to a state that is managed by an HCP with one or more operating pattern.

In some embodiments, a single data record may be represented in multiple tokens, each of which can have differing characteristics. For example, a token that is transmitted to a digital twin may differ from that received by a care signal processing system. Tokens may be constructed, for example, to have multiple layers, where for example the data in each layer may represent differing amounts of detail, historical information, temporal data and/or the like.

In some embodiments, such state may be in the form a session, where such a session is defined by, for example, time, events, inputs, outcomes, participants, locations and the like in any arrangement. Such a session can have a set of tokens as part of the session, for example representing data from sensors, devices, stakeholders and the like. A session may also include and/or have recourse to one or more token minting service, which can for example, produce tokens that are unique to that session and can represent data sets that are unique to the session, for example tokens that represent data sets, events, stakeholder interactions and the like that can only be created within that session. In this manner the occurrences of the various devices, events, patterns and/or pattern elements and/or stakeholder interactions may be represented by such tokens. These tokens, in some embodiments, may be passed one or more digital twin, which may act to form part of the session, such that the predictive and/or other care related capabilities of that digital twin can be incorporated in such a session for the benefit of the PUM and their current care and wellness condition. This can include one or more ML/AI predictive functions of a digital twin.

In some embodiments, the token set representing the data of a session, may be accessed based on the characteristics of the session, including the stakeholder invoking the session, the care condition of the session, any specifications that determine the session access, authorization and authentication for the session and the like.

In some embodiments a care hub may be employed for the generation of session tokens, representing the one or more states of patterns operating within an environment. This can include the aggregation, by reference and/or embedding of multiple token types into, for example multi segment tokens as representations of the state of one or more patterns.

Figure 3:
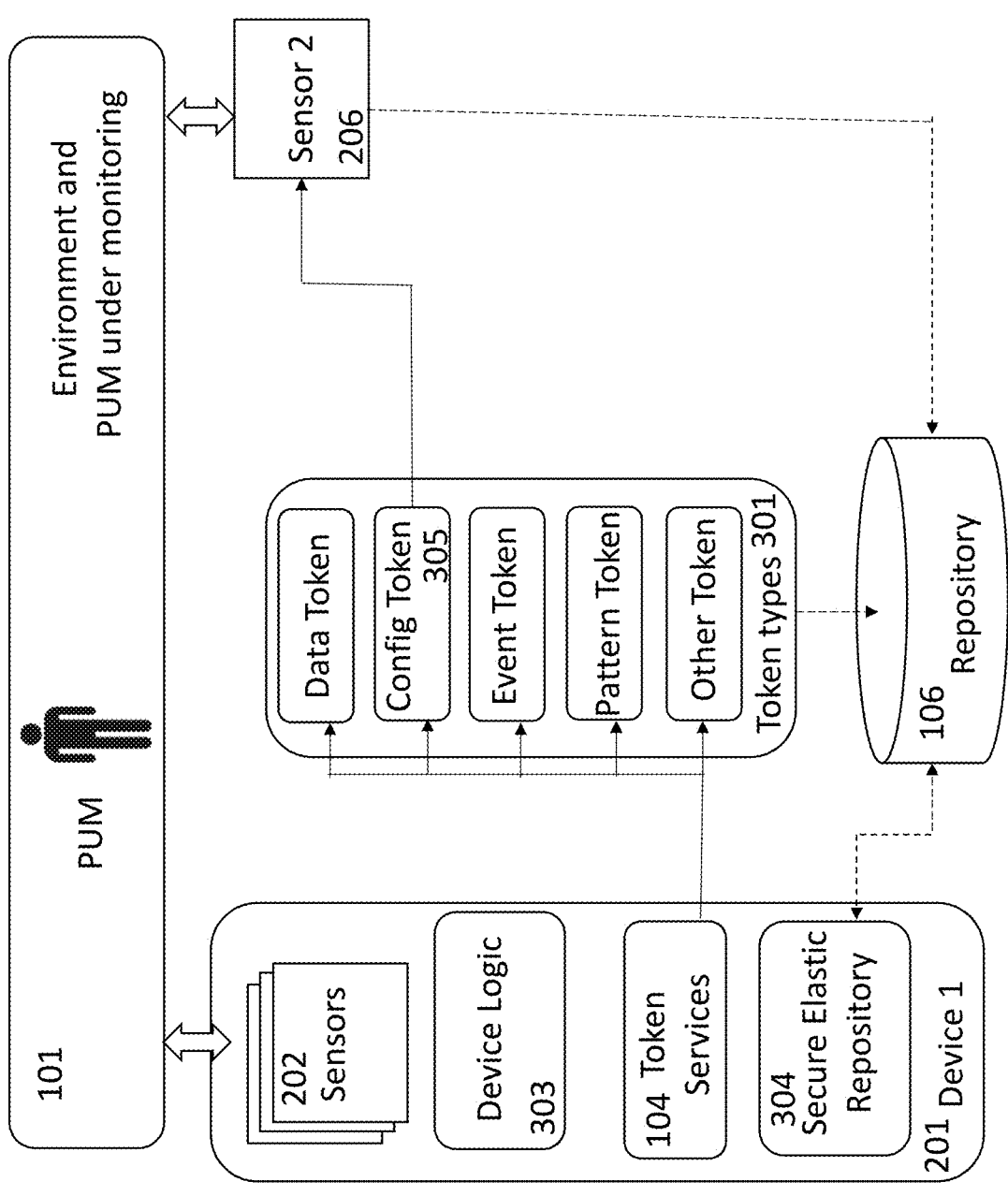
FIG. 3 illustrates a PUM in an environment under monitoring.

FIG. 3 illustrates a PUM in an environment under monitoring (101), which in part is being monitored by device 1 (201). This device includes one or more sensors (202), device logic (303), token services (104) and a secure elastic repository (304). In this example the token services may create one or more token of differing token types (301), depending on the capabilities and/or configuration of the token services (104). Shown here is a second sensor 2 (206) which receives a config token (305) which has been generated by device 11 (201) token services (104).

In some embodiments, where a session has been initiated, such a session may comprise one or more patterns and/or pattern elements, where for example a pattern representing a transition from one operating pattern to another, including predictive and/or transitional behaviors represented by such patterns and/or pattern elements can be represented by one or more tokens. For example, these tokens may then be passed to a suitably authorized stakeholder as the events and changes in the wellness condition of the PUM can be of interest to that stakeholder. For example, the stakeholder may be a medical professional, insurance company and/or relative.

In some embodiments in combination with one or more smart contract or other systemic representations, validation of a sequence of occurrences may be incorporated into a smart contract, for example represented by a token, so for example, the smart contract can access the token data set and undertake one or more programmatic process to verify the sequence of events and/or occurrences represented by the token, so as to for example, substantiate that such an occurrence exists, that is in occurred at the time and place, involved specific stakeholders, and included the specific events and occurrences and/or meets one or more specifications of such an event sequence.

Figure 12:
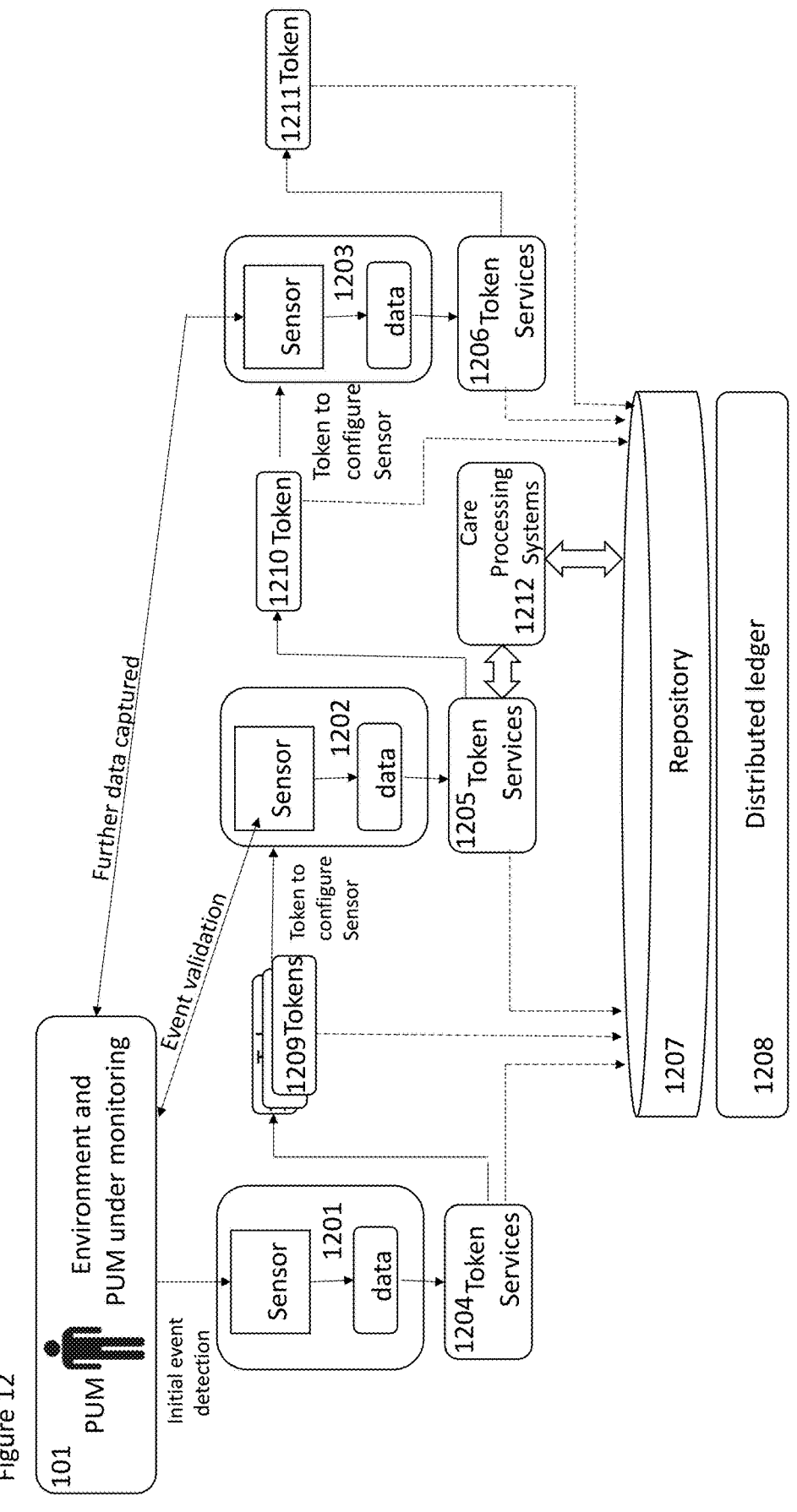
FIG. 12 illustrates a PUM in an environment under monitoring.

FIG. 12 illustrates a PUM in an environment under monitoring (101), where a first sensor and first data set (1201) are responsive to an event detection. In this example the event and data representing such event is securely communicated to a first token service (1204) which generates one or more tokens, for example data tokens, configuration tokens, event tokens and/or pattern tokens (1209). One of these tokens (1209) is a configuration token communicated to a second sensor set (1202), which configures this sensor set (1202) so as to generate data that can be evaluated for validation of the initial detected event. In this example a care processing system (1212) evaluates the data of second sensor set (1202) and instructs token services (1205) to create a further one or more tokens, in this case a configuration token, which is communicated to a third sensors set for the capture of further data sets from the PUM and their environment (101). In this example all tokens and the data of their creation is stored in a repository (1207), which is integrated with a distributed ledger (1208).

In many circumstances involving the well-being of a PUM, certain compliance data may be required to meet various conditions. Such conditions may be expressed by, for example, one or more stakeholders involved with that PUM. This can include insurance, care facility operators, friends and family, health professionals and the like. This compliance information can be represented as tokens, such that the receiver of the token is assured that the event, activity or other data represented by the token has occurred in compliance with the specifications. In some embodiments this can include the use of smart contracts and distributed ledgers.

In some embodiments, a windowed access to the data represented by a token may be used. For example, in the case of an emergency, data sets held by one or more tokens may be made available whilst the emergency is taking place, however when the situation is resolved, these tokens may then restrict certain of the data according to the prevailing specifications. For example, if the pattern transitions from a stable situation to an unstable one, i.e., in an emergency situation, the system may enable the tokens to be available and have data accessible to stakeholders involved in such emergency, for example paramedics and the like. In some embodiments, such an emergency may for a session for which tokens are created, where different stakeholders may access, in whole or in part data sets accessible by the token, depending on their identity. This can include their devices having access to the data; however, the data may only be available for the time period of the emergency. This for example may be enabled by the use of at least one application, cloud service, digital twin and the like. There can also be a persistent record, for example for an audit trail, digital twin, distributed ledger and the like. In some embodiments a token may be accessible through the provision of a specific key, authentication indicia or other enablement, that supports the access to the date for a specified set of circumstances. This can include, for example, time, locations, proximity of stakeholders and/or specific equipment or facilities, identity of one or more stakeholders, one or more data sensor sets, one or more patterns and the like. These specifications may be represented by a further token such that, for example, an application, device and/or system may require both tokens, the one containing data of the PUM and the authorized access token to be collocated within a particular time period for that access to be provided.

Tokens for Sensors, Devices and/or Systems

In some embodiments, each of the sensors, devices, systems and stakeholders have a unique identity. Although this identity may be self-assigned and/or provided by a system service, within the network in which the sensor, device and/or system operates this identity is unique.

In some embodiments a token can be a binary and/or a text string uniquely referencing a record, stored separately, for example, in a database system, which can control access to it, which are described as lightweight tokens. In other embodiments a token can be a binary and/or a text string containing the data, usually in a digitally signed and encrypted form. For example, one common implementation of such kind of tokens is JSON Web Token (JWT), which contains a signed and encrypted JSON-formatted object. A JWT token consists of three parts: a header, a payload, and a signature. The header contains information about the algorithm used to sign the token, and the payload contains the relevant data, in some embodiments, usually user authentication and access information. The signature is used to verify that the token was not tampered with during transmission.

In some embodiments a token can be a combination of the two approaches, referencing and containing data. For example, a JWT token can be created with a payload that contains part of the PUM data, as well as one or more references to additional PUM data, stored separately. For example, sensor, device and/or system data may form part of the payload, as may configuration data for one or more sensors, devices and/or systems.

In some embodiments this may involve configuration of the end points of such communications so as to access the multiple token segments. Such configuration may use one or more proprietary algorithms and/or encryption techniques so as to enable only those end points authorized to access such data.

Figure 20:
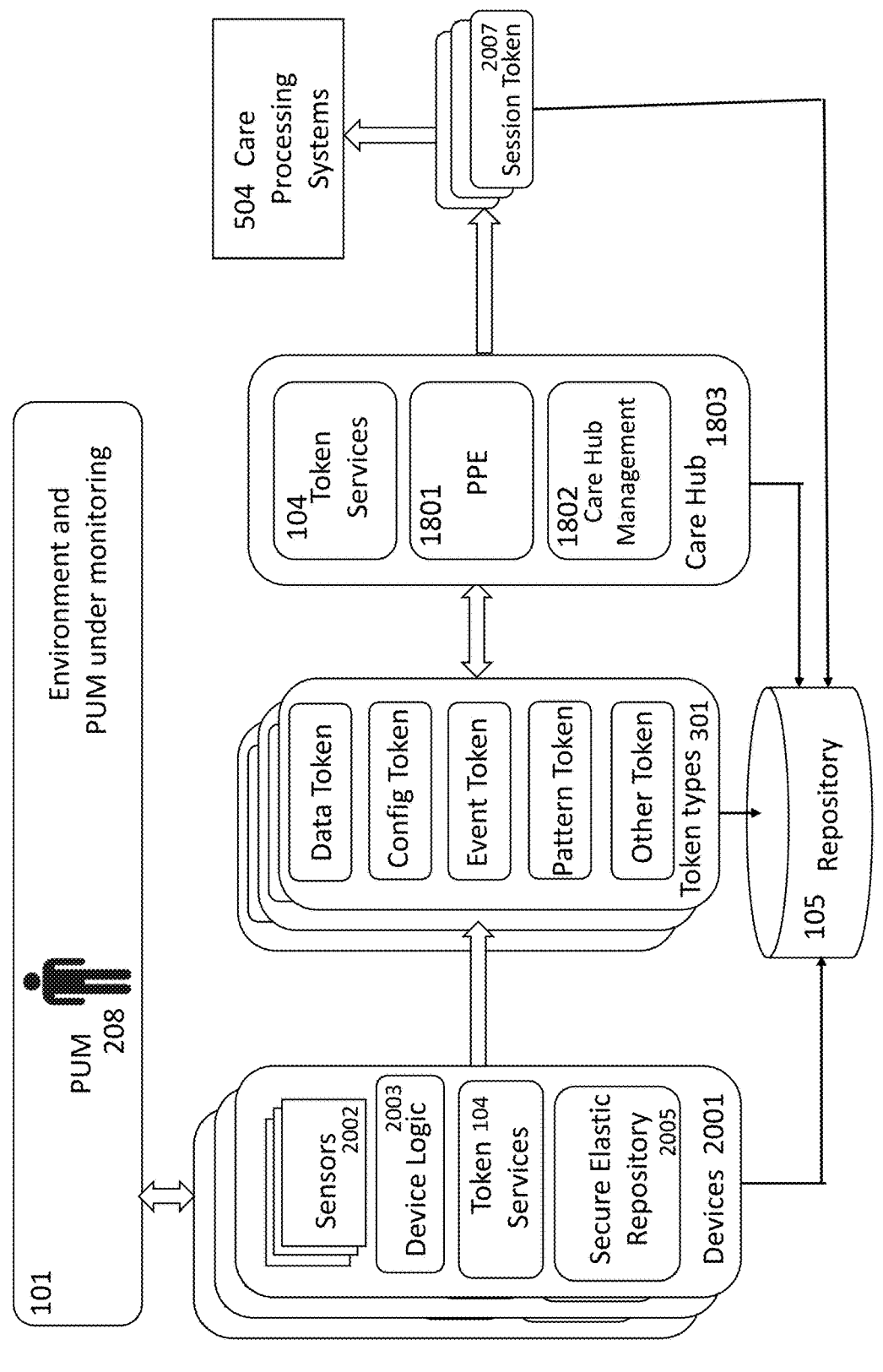
FIG. 20 illustrates a set of devices.

FIG. 20 illustrates a set of devices (2001), comprising at least in part, sensors (2002), device logic (2003), token services (104), secure elastic repository (2005), which are engaged in monitoring a PUM (208) in an environment (101), resulting in the generation of data sets represented by tokens of differing types (301) which are communicated to a care hub (1803) comprising at least in part token services (104), PPE (1801) and care hub management (1802) configured to generate a set of session tokens (2007) which represent the state of the patterns operating for such monitoring. In this example such sessions tokens (2007) are communicated to a care processing system. In this example, each of the devices (2001), token types (2006), care hub (1803) and session tokens (2007) are stored by reference or embedding in a repository (105)

Multi-Segment Tokens

In some embodiments, a token may comprise a set of segments, each of which can have a differing access method. Such multi segment tokens can include binary and/or a text string uniquely referencing a record, by reference or embedding. The configuration of a token and one or more end points can include configuration so as that only specific end points may be able to access specified segments of a multi segment token, for example in a token with, for example, 5 segments, different end points may only be able to access, for example segment 3 or 5.

Figure 10:
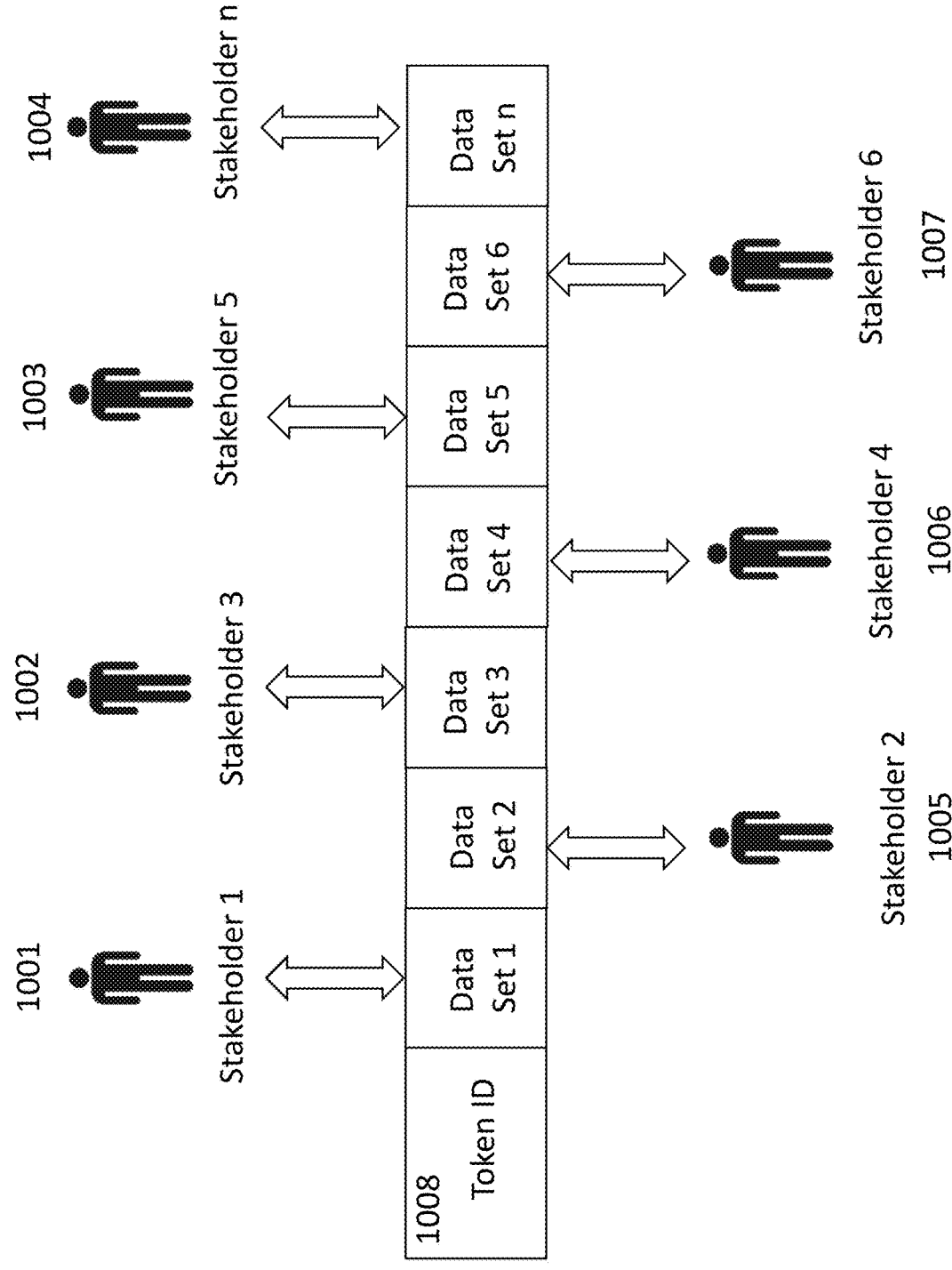
FIG. 10 illustrates a multi segment token comprising one or more token ID and multiple data sets.

FIG. 10 illustrates a multi segment token (1008) comprising one or more token ID and multiple data sets, where each data set is available to specific stakeholders (1001 . . . 1007). Decentralized tokens are created and managed on a decentralized network, such as a blockchain or other type of digital ledger. Unlike traditional tokens, which are created and managed by a central device or a central authority, decentralized tokens are created and managed by a decentralized network of devices and/or users following a set of rules for consensus and security. One of the key benefits of decentralized tokens is that they are trustless, not requiring a centralized entity to verify or validate their creation and access. Instead, tokens and their related transactions are verified and validated by the decentralized network itself, using complex algorithms and consensus mechanisms. Decentralized tokens are often used as a means of exchange or as a store of value, such as currency, securities, property, or even virtual goods in online games. However, they are also useful for storing, representing and/or exchanging information in a way that is secure and verifiable. For example, the representation and distribution of PUM care and wellness data, where the privacy of the PUM and the security of the data regarding the PUM is well served by such an approach.

In some embodiments, a common method for creating decentralized tokens is by using a variety of public blockchain platforms, such as Bitcoin, Ethereum or Binance Smart Chain, or a private or permissioned blockchain. The data represented by the token can be stored in the distributed ledger itself (on-chain storage) or in an external storage system, such as a database, having the ledger hold the reference to such externally stored data (off-chain). A combination of on-chain and off-chain data storage may also be used.

In some embodiments, tokens can also be issued and managed by a single entity, operating as a centralized service, such as a sensor, device, system, a care hub or other computing subsystem. These can hold data in local storage and/or database(s) and/or in an external storage and/or a repository system in any arrangement.

Figure 8:
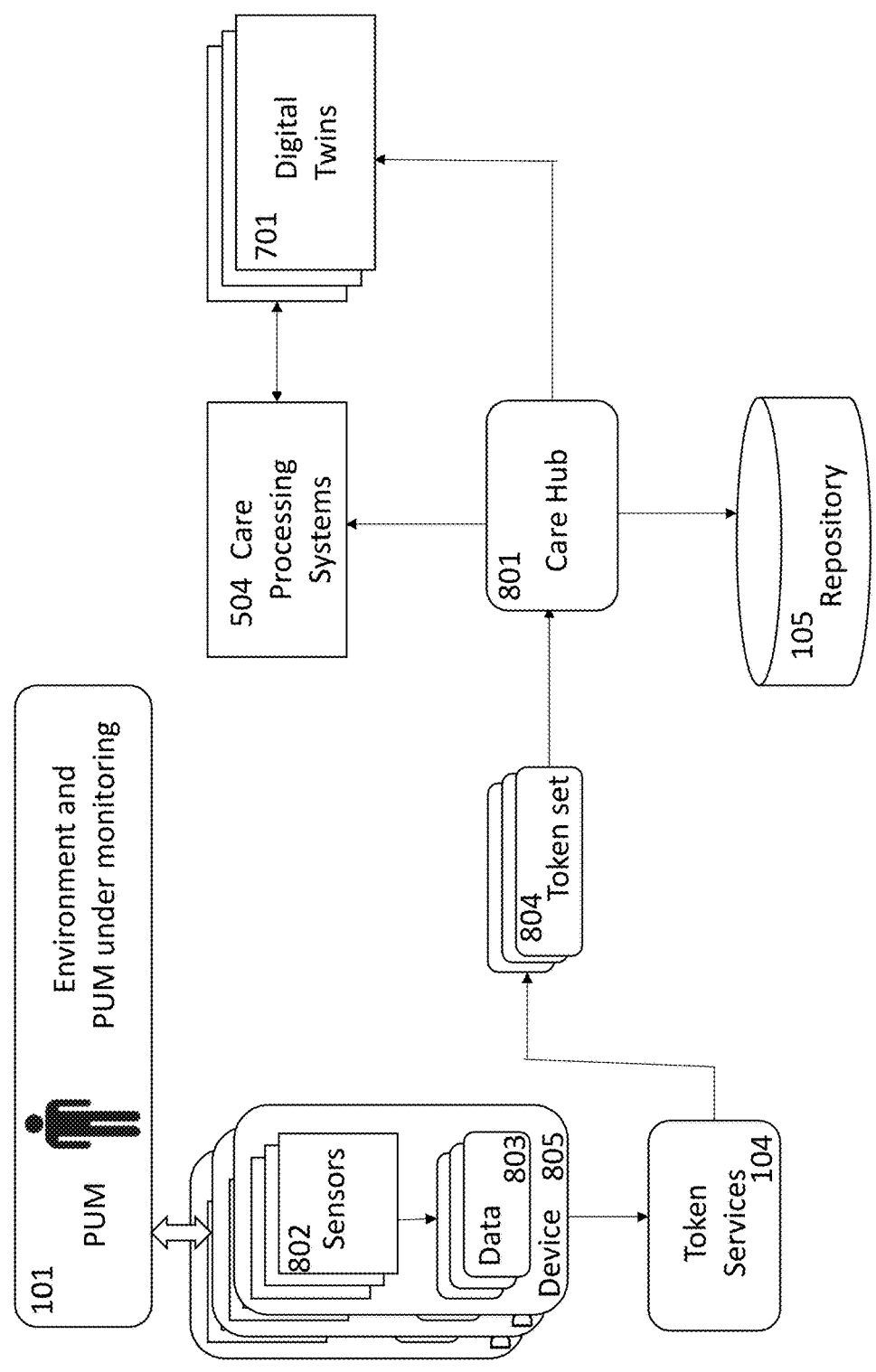
FIG. 8 illustrates a PUM in a monitored environment.

FIG. 8 illustrates a PUM in a monitored environment (101), where one or more devices (805) comprising sensors (802) generating data (803) are, at least in part, monitoring the PUM and/or the environment (101). In this example, data (803) is securely communicated to token services (104), which generates token set (804) which is communicated to care hub (801). Care hub, for example, can then transmit tokens to repository (105), care processing systems (504) and/or digital twins (701), in any arrangement.

In some embodiments, a device, such a sensor device and/or system, for example, a care hub, may directly issue a token that holds or references data that the sensor, device and/or system produces and/or stores through refence or embedding. The sensor, device and/or system may also use an external token issuing system to create the token.

The creation and issuing of such tokens may be based on one or more thresholds, time periods, event, actions responses and/or other specification. This can include one or more authorizations for the issuing of one or more tokens and may include specification of the one or more end points able to access the data payload of the token. In the example where the token is a refence, for example, a token indicating that a specific event has occurred, for example that a carer attended a PUM at a specific location for a period of time, the data payload of the token is the token itself, and as such the end point will have the appropriate methods for extracting the payload. This can include one or more thresholds that may form and/or be based on the multi-dimensional feature set to which the sensor, device and/or system is contributing.

In some embodiments, tokens that comprise data in an encrypted form can be resolved by any device that has access to the decryption key. A public key mechanism, such as Rivest-Shamir-Adleman (RSA) or Elliptic Curve Cryptography (ECC), can be used to exchange tokens securely. For tokens issued by a specific sensor, device and/or system, including for example a care hub, that contain references to externally stored data, the external storage subsystems may provide access control mechanisms, which can be based on authentication/authorization schemes and/or may be combined with other control parameters such as time and location and the like.

Decentralized tokens, such as those based on blockchain, may be combined with smart contracts running in the blockchain's protected computing environment to provide access control to the token-referenced data.

In some embodiments one or more Bearer Tokens sensors, devices and/or systems can be biometrically bonded to PUM or other stakeholder such that a bearer token is created and managed by such sensor, device and/or system. Such a bearer token is a representative of a PUM, such that in in certain circumstances or situations, the possession of the bearer token can support one or more operations and/or interactions. In some embodiments such bearer token may form part of the identity of a PUM or other stakeholder.

In some embodiments, the emergence of practical quantum computers has the potential to break many of the encryption methods currently in use, including RSA and ECC. Some embodiments may use quantum-resistant or post-quantum cryptography, such as Lattice-based cryptography, as part of the implementation of centralized or decentralized token issuing and resolution mechanisms.

Figure 4:
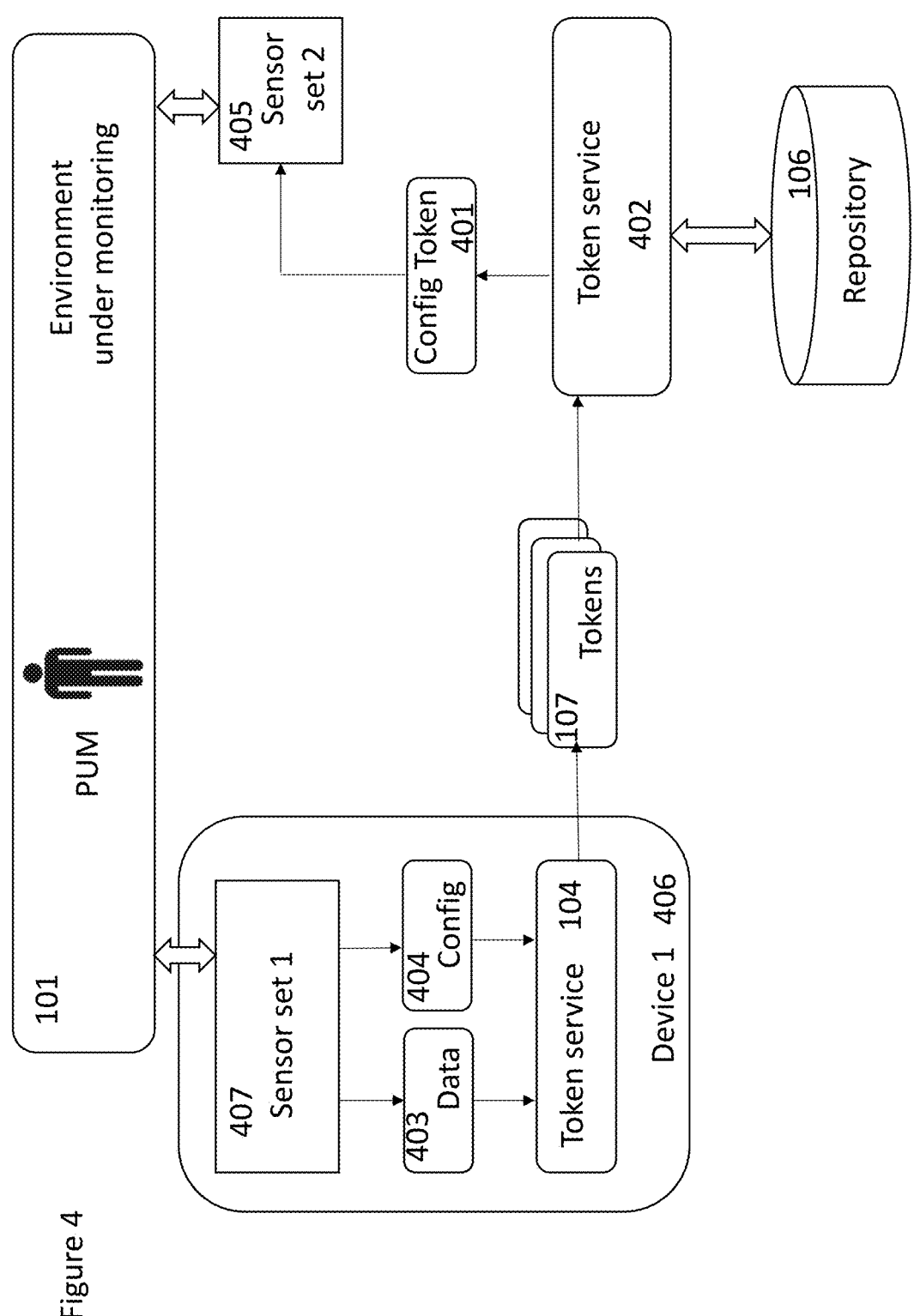
FIG. 4 illustrates a PUM under monitoring in an environment.

FIG. 4 illustrates a PUM under monitoring in an environment (101), that is in part monitored by device 1 (406), which at least in part comprises sensor set 1 (407), which can generate sensed data (403) and configuration data (404), both of which are provided to token service (104). In this example token service creates a set of tokens (107) which are communicated to a further token service (402), which for example may extract the configuration data represented by the tokens (107) and generate a configuration token (401) which is communicated to second sensor set (405) which in monitoring PUM and environment (101). In this example token services (402) may store tokens (107) in a repository (106).

One aspect of the system is the use of tokens to represent the characteristics, including capabilities, configuration, and identity, of a sensor, device and/or system. This supports the privacy of the capabilities of these devices, such that only authorized identities may access these characteristics represented by the token. This can include the specifications, including for example API calls, of the interface for these sensors, devices and/or systems such that configurations of the sensors, devices and/or systems and/or access to data sets generated by such may be undertaken by authenticated and authorized entities. This can involve, in some embodiments a preemptive exchange of tokens between two or more sensors, devices and/or systems to establish an authenticated and authorized by all party's relationship. Such relationships may be established directly and/or with third party services and may include the use of, for example, public key encryption. In some embodiments such configurations may be stored by the device, either through embedding in the device storage or through use of a connected storage capability. In this example, the selection of configurations for a device and/or sensor can be undertaken by an authorized entity through the use of tokens representing those configurations. The token may also represent the state of a device, including for example the monitoring of an environment and a PUM, such that this data set represented by a token can then be communicated to, for example, a care signal processing system, which may then invoke one or more processes.

In some embodiments the preset device configurations may be the only manner in which to change the operations of the devices and/or sensors such that even if the device/sensor has capabilities outside of those specified in the configuration, for example video, ability to record audio and the like, the configuration may limit the use of such characteristics to enable and/or enforce privacy of a PUM, environment and/or other stakeholder.

These inherent characteristics of devices and/or sensors can be made available in any combination to one or more systems and/or elements thereof, such as for example a care signal processing system, however the use of tokens as representations of the data that they can create, store, manage and/or transmit provides the ability to effectively manage the degree to which this data is made available to the authorized recipients, such as for example a care signal processing system, one or more operating patterns, HCP and/or devices, digital twins and the like that are operating in a care monitoring manner.

Figure 16:
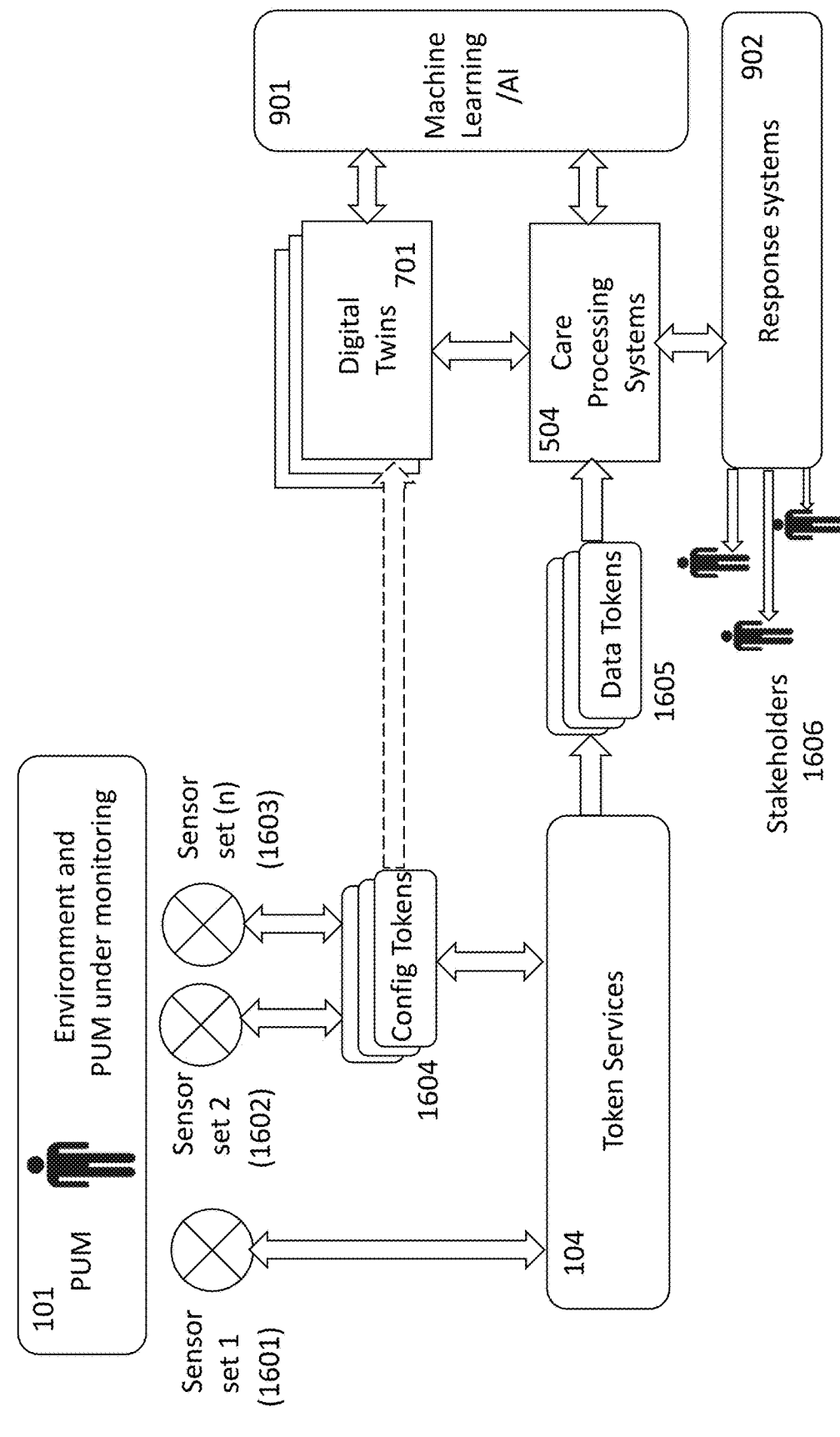
FIG. 16 Illustrates a PUM and environment under monitoring.

FIG. 16 illustrates a PUM and environment under monitoring (101), where sets of sensors, (1601, 1602, 1603) are monitoring the environment and PUM. In this example a token service (104), generates and issues tokens for sensor sets 1601. Sensors sets (1602,1603), in this example include a token services module, which generates, for example, configuration tokens (1604), which are communicated to the external to those sensor sets tokens services (104). In this example, configuration tokens (1604) are communicated, potentially on demand and/or dynamically to one or more digital twins (701), where such configurations may be deployed within one or more digital twin for the evaluation, for example by care processing systems (504), using in part machine learning/AI modules (901). Such evaluation may be used to determine, in whole or in part, behavior or pattern variations for the PUM. This can result in outputs which are communicated to a response system (902). In some embodiments, response systems may provide alerts or other messages to one or more stakeholders (1606).

In some embodiments, each sensor, device and/or system may have a privacy profile, for example an ACL, set of specifications, authorized relationships and the like, represented by one or more tokens. This profile can be created by for example, the owner of that device, including the PUM, operator of a care facility, authorized care village stakeholder, such as a medical professional, emergency service, including operatives thereof, and the like.

In some embodiments such settings may be overridden by an authorized entity, where the situation is deemed to be of a nature that requires the data that is specified to be private, to be made available for a specific time and/or event, such as an emergency, where care and well-being of a PUM is at significant risk.

Tokens and Privacy

The determination of what data is considered private can be of significant consequence to the one or more various stakeholders within a care village. There may be no common, amongst the stakeholders and/or systems, agreed perspective on the set of data that a stakeholder may consider private. Each stakeholder may wish to ensure that certain data is held in private and/or retained in private by them, so that those certain data are not available to other stakeholders and/or any other person, entity or system in any specified timeframe.

This is particularly important when dealing with the personal health condition of a PUM, as well as their medical health records, financial information and/or other matters that either they deem, or are mandated by one or more legal statutes, such as HIPAA, PII, to be private data.

The challenge is to ensure that, within the context of provision of monitoring of and for the wellness and care of a PUM, only the pertinent data is available to those stakeholders providing the monitoring and/or care and wellness in a manner that optimizes the potential care and wellness outcomes for the person under care. For example, notification of critical allergies can be essential for an Emergency Medical Technician (EMT). A further aspect is ensuring that data sets employed for the provision and support of care and wellness are only retained by the stakeholders requiring such data for the period of the provision and/or support of the care and wellness of the PUM. However, there may be need to create a record, in the form of an audit trail that provides evidentiary proof of that provision and support by the stakeholders involved at the time and location of such events. To this end a token may be employed to provide, for example in the form of a record written to one or more distributed ledger, such an immutable record, without revealing the full details, for example in the form of the data sets involved, of such provision and/or support, except to authorized and authenticated stakeholders, such as medical professionals, for example a medical doctor.

Figure 11:
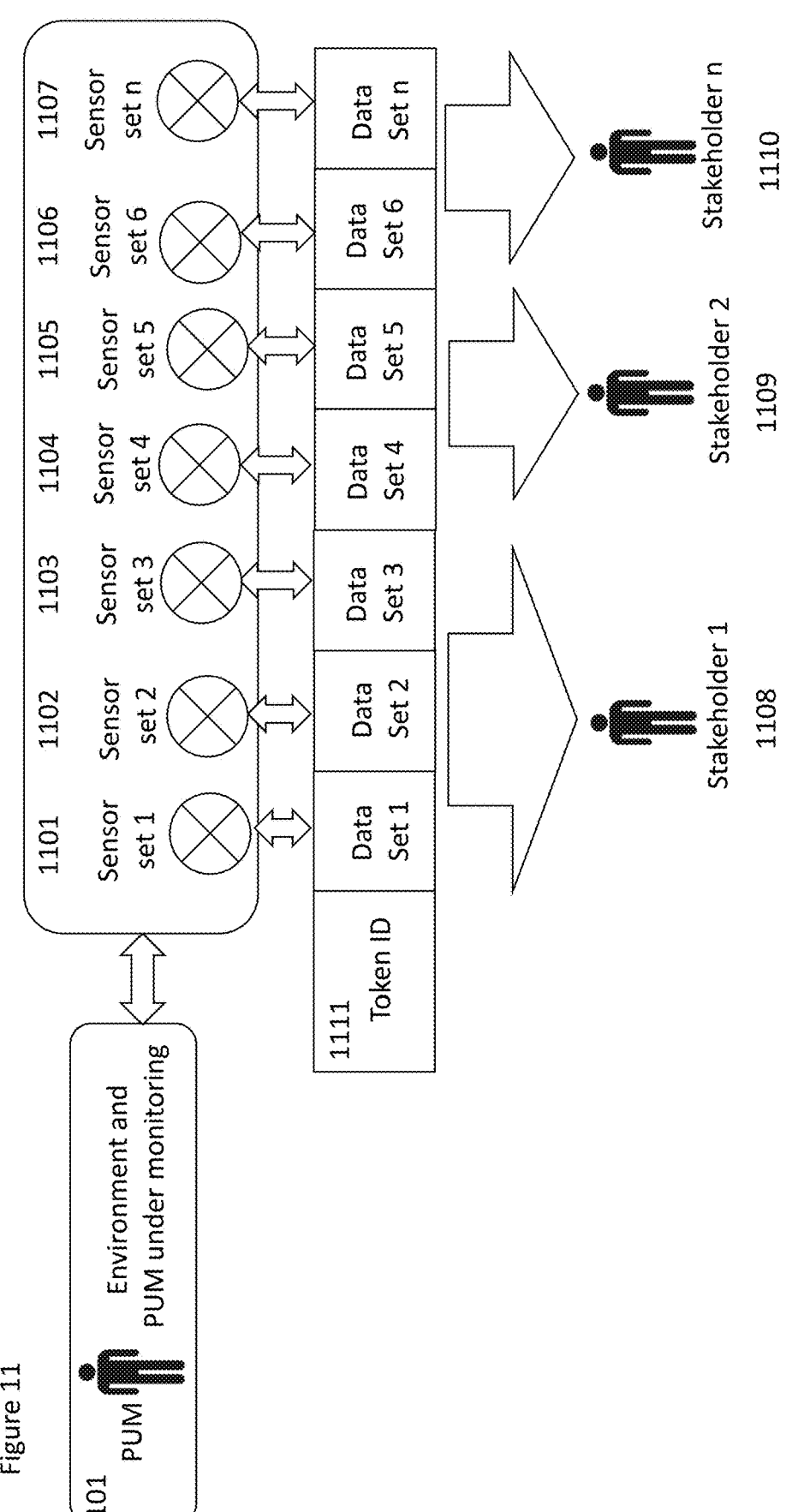
FIG. 11 illustrates a set of sensors which are involved in monitoring a PUM in a monitored environment.

FIG. 11 illustrates a set of sensors (1101-1107) which are involved in monitoring a PUM in a monitored environment (101), where data sets from these sensor sets form part of a multi segment token (1111), such that only specific stakeholders (1108, 1109, 1110) receive specific data sets from specific sensors. For example, stakeholder 1 (1108) has access to data sets 1, 2 and 3 only.

The use of tokens provides a means to enable such a data privacy facilitation, whilst ensuring that the data made available are only those data that are essential to the care and wellness condition management required at the time.

Figure 5:
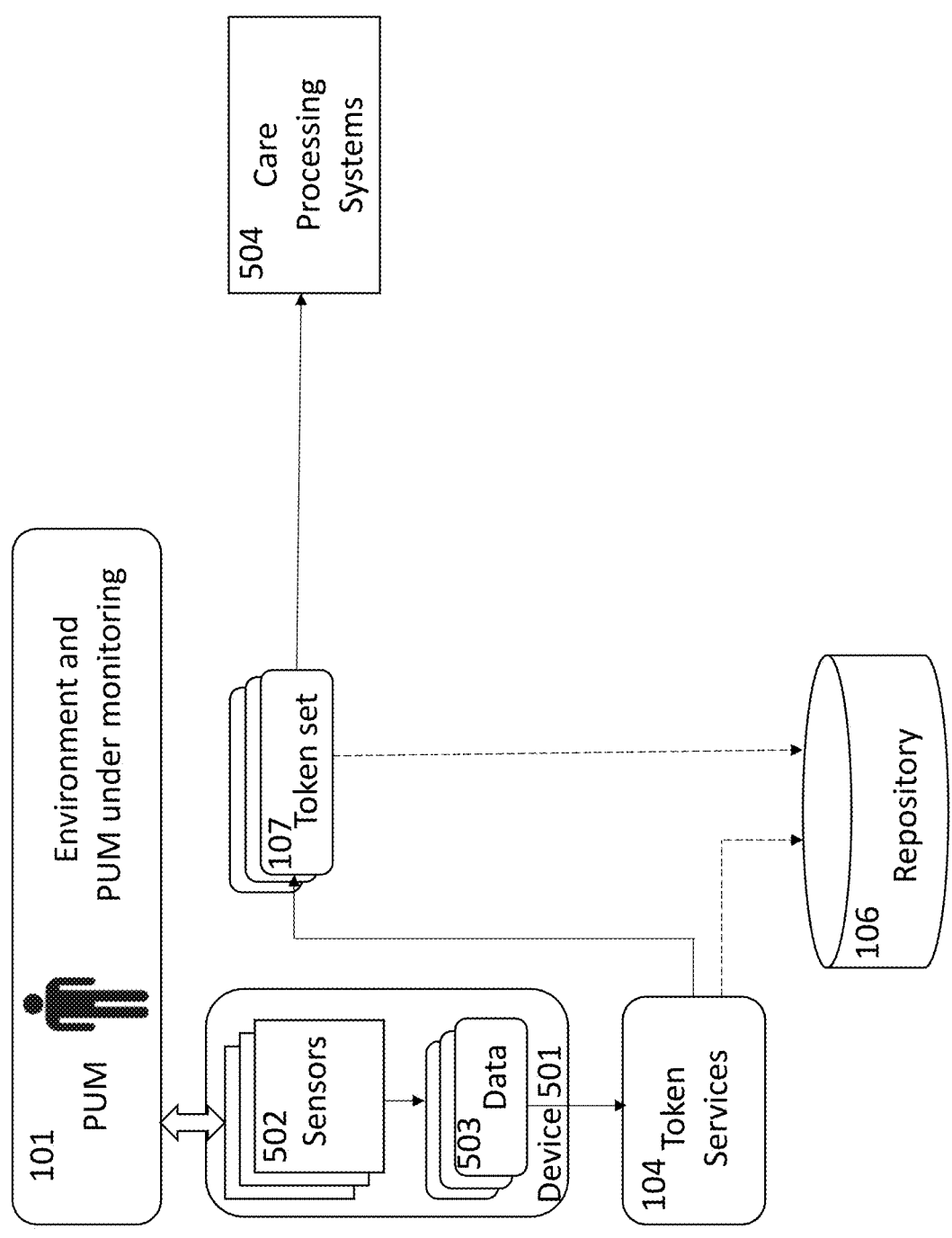
FIG. 5 illustrates a PUM in an environment.

FIG. 5 illustrates a PUM in an environment (101), which is in part monitored by a Device (501), comprising sensors (502) generating data (503), which is then communicated to token services (104) that in turn generates a token set (107), which is then communicated to care processing systems (504).

In some embodiments, data may be transferred to one or more digital twin in support of predictive systems which can include one or more machine learning processing modules. For example, a digital twin may be instanced to anticipate one or more future care and wellness conditions of a PUM, based, at least in part, on the HCP and operating patterns of that PUM. In this example, the digital twin may represent a set of possible future care and wellness states for the PUM, where such predictions are based, at least in part on the data sets provided by one or more sensors, devices and/or systems that are involved in monitoring a PUM. In some embodiments, such data sets may be attributable to one or more PUM with a specific operating pattern within an HCP, where the specific identity, location or other PII is not revealed to the digital twin. This can involve data sets that could be distributed to stakeholders through tokens.

Figure 17:
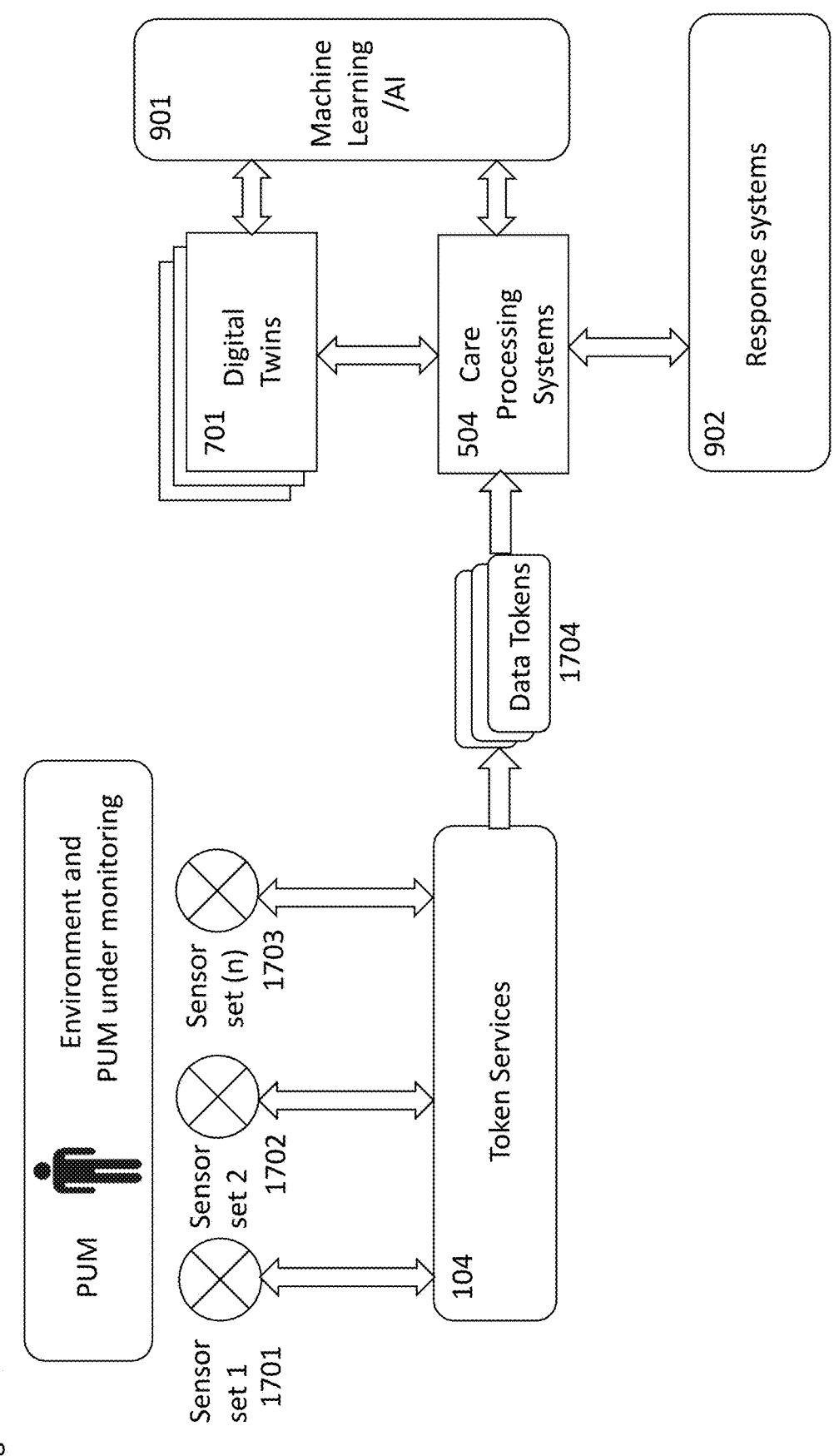
FIG. 17 illustrates a PUM in an environment under monitoring.

FIG. 17 illustrates a PUM in an environment under monitoring (101), where one or more sensors sets (1701, 1702,1703) generate one or more data sets, which in part include configuration data, that is securely communicated to token services (104). In this example, token services (104) generate a set of tokens (1704) representing the data received form the sensors (1701,1702,1703), which are communicated to care processing systems (504). Care processing (504) may then invoke digital twins (701) and/or machine learning/AI modules (901) in support of one or more instructions to response systems (902).

A digital twin can represent the care and wellness state of a PUM and their environment with sufficient fidelity so as to be used in predictive analytics, including the use of machine learning, for the care and wellness benefit of the PUM. In many circumstances the digital twin can be one of a set of digital twins representing a set of PUM that have a common set of care and wellness characteristics, such as the same or similar HCP and the operating patterns and pattern elements thereof. The degree of disclosure of the data sets pertaining to a PUM to a digital twin is to be sufficient for the Digital Twin and any associated analytic and/or predictive processing to be able to undertake effective predictive, trend, underlying care framework identification and/or other care and wellness benefit processing. This can be achieved in a number of ways, employing differing embodiments, for example the tokens may include a set of specifications that can be interpreted by a suitably authorized digital twin that can access, potentially on a time and/or function limited basis the data that is deemed private by a PUM for a specified purpose. This type of disclosure may be agreed by a PUM in advance. The data received by the digital twin may be expunged after the appropriate analytics and/or processing has been undertaken. In some embodiments the digital twin may operate as a proxy for a PUM, such that all data is available to a digital twin, and the digital twin acts as the privacy guardian of the PUM, enacting and enforcing the privacy choices of the PUM. In a further embodiment, there may be tokens that are digital twin specific and include further specifications determining the use, propagation and/or configuration of the tokens and the digital twin operating upon them.

A key aspect is that the digital twin, though one or more configuration, retains the trust relationship with the PUM, such that the data a PUM deems private remains so, and yet the digital twin can function to support the care and wellness monitoring of that PUM to the benefit of the PUM.

Figure 7:
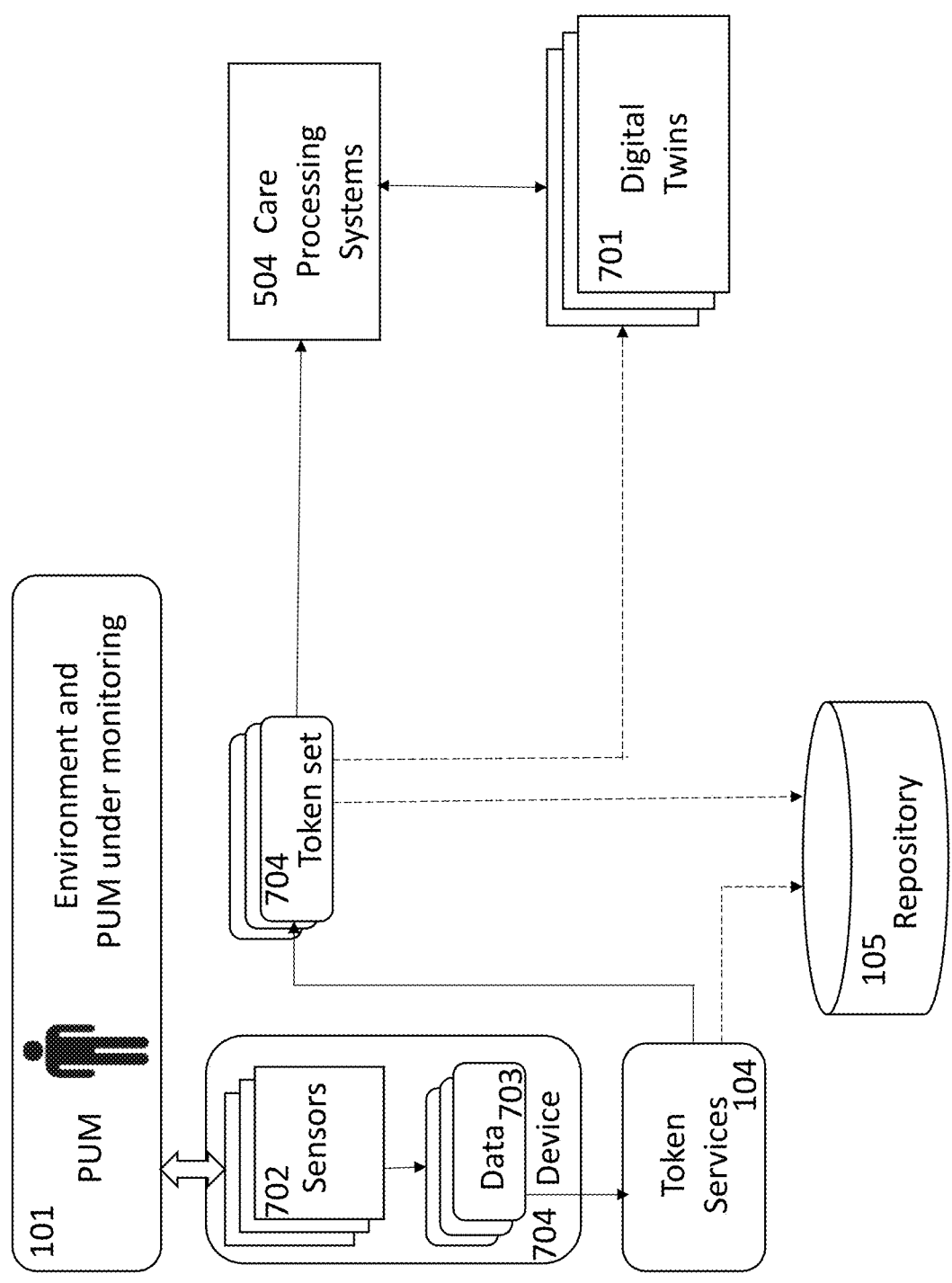
FIG. 7 illustrates a PUM under monitoring in an environment.

FIG. 7 illustrates a PUM under monitoring in an environment (101), which is monitored, at least in part by a device (705), which comprises, at least in part, sensors (702) that generate data (703) representing the PUM and environment under monitoring (101). In this example the data (703) is communicated securely to token services (104), which generates a token set 704). The token services may communicate, in whole or in part the data represented by the tokens (704) and/or the data comprising such tokens and/or the processes of the generation of such tokens to a suitable repository (105). In this example the tokens are communicated to care processing systems (504), which can then communicate the tokens and/or the data represented by the tokens to one or more digital twins. In some embodiments the tokens (704) may be communicated directly to the digital twins (701).

In some embodiments, a distributed ledger systems, such as Ethereum, can be deployed to support this systemic functionality. For example, this can include a virtual computing environment that can maintain states and execute arbitrary machine code and can combine ledger data with external inputs to provide output and/or modify the state of the distributed ledger based on the codified logic or calculations, known as smart contracts, all within the protected network-distributed computing environment. This can be combined with tokens in order to enable functions such as selective translation of tokens into the data sets, they represent, based on access rights of the caller, interpretation of a token (from token to its meaning within the context of the caller), creation of new tokens from combination of input tokens and data within the Distributed Ledger. Combinations of these functionalities can be used in smart contracts that run transactions and to provide information and services without exposing private or critical information or functionality to unauthorized stakeholders, within a highly secure environment and without limiting the availability of functionality necessary for care and wellness monitoring and response.

In some embodiments one or more smart contracts can be used to validate PUM-related data sets, such as those created by one or more sensors, events, tokens and/or aggregations before they are stored in a distributed ledger. This may include data sets that can be used for Machine Leaning model training and/or for digital twin-based modeling and/or simulation, to improve efficiency, transparency, accuracy and/or quality of one or more Machine Learning processes and/or one or more digital twins predictions, inferences and/or other results.

In some embodiments there may be one or more protected processing environment (PPE), which can undertake evaluation and/or processing of one or more data sets represented by one or more tokens in a secure manner. In this sense the protected processing environment becomes for the period of the processing of such token data an extension to the token, such that the conditions of the token, expressed as specifications, are respected and/or enforced by the PPE. PPE may be dynamically instantiated by, for example, the environment sensing systems, including sensors, devices and/or systems thereof, care signal processing systems and/or other authorized care village system elements, for example those managing at least one care village. These PPE can create further tokens representing the data that the PPE operates upon and can, for example store such data in a repository, such as a secure repository for that PPE and/or in a distributed ledger.

Figure 13:
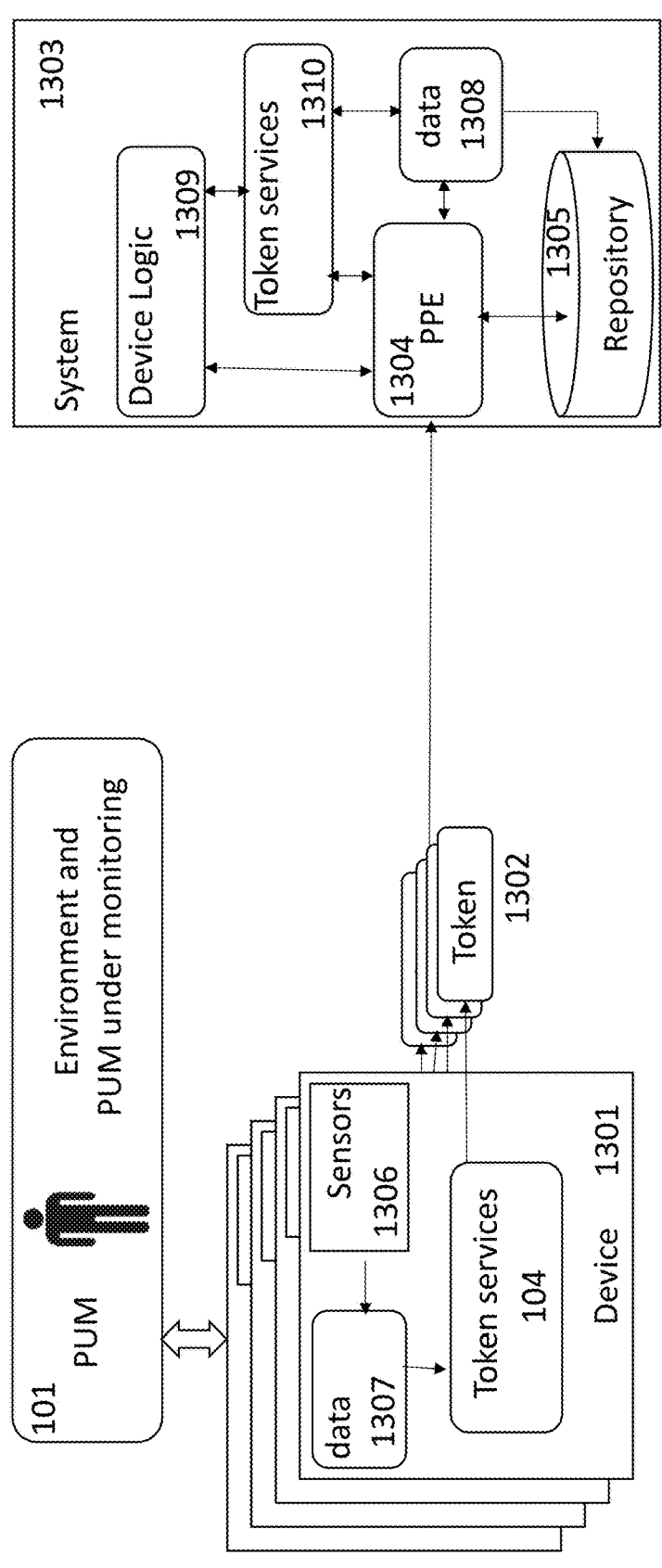
FIG. 13 illustrates a PUM in a monitored environment.

FIG. 13 illustrates a PUM in a monitored environment (101), where a set of devices (1301) comprising, at least in part, sensors (1306) and data (1307) communicate such data to token services (104), which generates tokens (1302). In this example tokens (1302) are communicated to a system (1303) that comprises, at least in part, one or more PPE (protected processing environment) (1304), where in combination with token services (1310) and/or device logic (1309), one or more tokens and the data they represent (1308) may be processed in a secure and protected manner. In this example, tokens, processing, device logic and/or token services operations and data may be stored in a repository (1305). In some embodiments, such a system (1303) may be embedded in one or more devices (1301) and/or may be invoked by such device through, for example a cloud service.

A digital twin can provide at least in part, a virtual environment for a stakeholder of a care village to interact with, for example for training, practice, anonymized interactions and the like. In some embodiments, the system may use predictive caching, for example using a digital twin for a PUM to evaluate that if the likelihood of an event, for example a fall, coughing fit, shortness of breath and the like, is above one or more threshold, for example as represented by a multi-dimensional feature set, then one or more stakeholders may be alerted, for example via their device and can receive an alert and/or be pre-loaded with data sets that are pertinent to the predicted and/or anticipated care and wellness situation. This data may be in the form of a token, which for example, may then only be available when the stakeholder and device are in proximity to the PUM, where such PUM may also have a device, such as a PERS and/or other carried or wearable device, or where the PUM and stakeholder are engaged, locally or remotely in a care and wellness related activity. Should the situation occur for which the data has been preloaded, then the data can be made available, however if the situation does not eventuate, then that data set will remain unavailable.

In some embodiments, blind signatures may be used as part of a token in part or in whole. The use of blinding may support various privacy schemas, including those of sensors, devices and/or systems. For example, data collected by a sensor may be provided, for example, encrypted or unencrypted, to any number of other authenticated and/or authorized sensors, services, systems and/or devices, however the identity of the originating sensor and/or the PUM may be blinded so as to protect the privacy of this source and/or the PUM.

Privacy can be configured on a sensor-by-sensor, device by device and/or system by system basis, such that each sensor, device and/or system can store data collected by such a sensor, device and/or system and transfer such data to one or more repository in a secure manner. The repository may be part, for example incorporated within such sensor, device and/or system, of the sensor, device and/or system that includes the sensor, device and/or system and/or may be a repository securely connected to that sensor, device and/or system through one or more communications methods. This can include the use of tokens as, in whole or in part, the communications method, whereby each token can be configured to represent one or more data sets and/or the originating sensor, device and/or system identity, such that the transfer of the token can only be between the sensors, devices, and/or systems and/or other sensors, devices and/or systems that are authenticated by the originating sensor, device and/or system. The security for such transfer can be implemented using cryptographic methods, including PKI, and may include the use of blind signatures.

In some embodiments a sensor may generate a token based on a data set created by the sensor, which is immediately transferred to an appropriately authorized and authenticated other sensor, device and/or system, such that the originating sensor does not retain the data set created. In this manner such a sensor retains no record of the data set. In some embodiments, a sensor may not retain any of the generated data sets, it may however retain and/or transmit a record of the transfer of that data set to another sensor, device and/or system. For example, this may be in the form of a token comprising the identity of the originating sensor, device and/or system, temporal data, such as time and duration of transfer, identity of the originator and receiver and/or an acknowledgement of receipt of such transfer by the receiving party.

Figure 6:
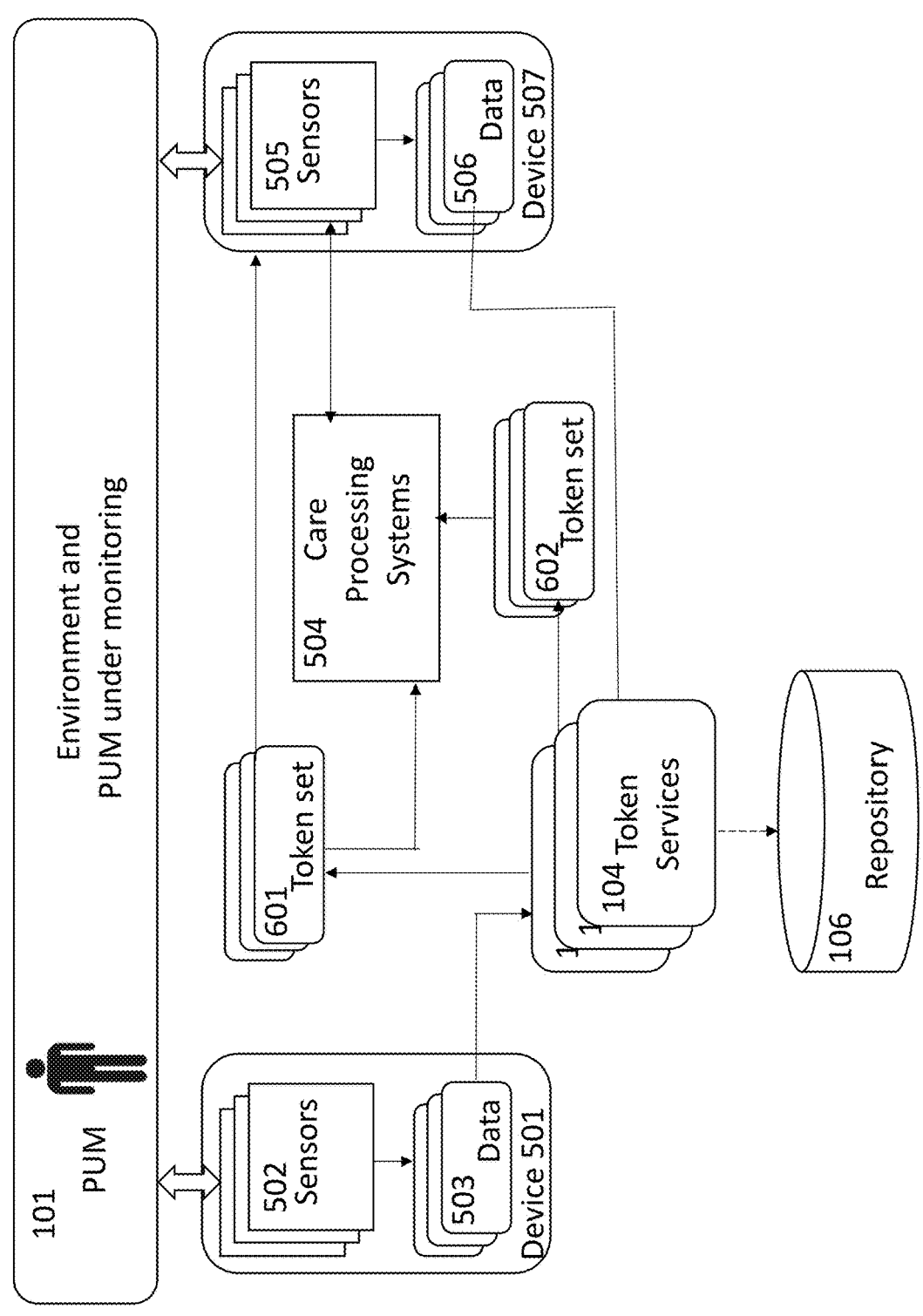
FIG. 6 illustrates a PUM in an environment under monitoring.

FIG. 6 illustrates a PUM in an environment under monitoring (101), where multiple devices, (501,507) comprising respectively multiple sensors sets (502, 505), generating multiple data sets (503,506). In this example these data sets (503,506) are securely communicated to token services (104), which generates token sets (601,602), representing those data sets. These in turn are communicated to care processing systems (504), which in this example may communicate with one or more sensors sets, for example, sensors (505), with one or more tokens and/or data represented by such tokens.

In some embodiments, a sensor may generate one or more data sets, which can then be processed by such a sensor and/or a secure proxy processor for that sensor. This can include the incorporation of such data sets into multidimensional feature sets, where processing, such as care signal processing, may be employed to identify and/or recognize one or more events and/or event sequences, that in whole or in part are part of one or more patterns, including operating patterns and/or pattern elements within an HCP for one or more PUM. These data sets which represent the one or more events and/or event sequences, may then be retained by a sensor, device and/or system, in whole or in part and/or may be transmitted and/or transferred to one or more other sensors, device and/or system. In some circumstances, for example in the case of geo-fencing, the retained data may be made available to other systems, for example a care signal processing system, for example if that data is requested by such a system and/or the configuration of the sensor is such that the data is provided to the care signal processing system on a timed, demand or request basis. In some embodiments, retention of these data sets may be configured by one or more sensors, devices and/or systems such that the data may be stored for a specified time period and/or then either transferred to one or more other sensors, devices and/or systems and/or erased or discarded. The recordation of the sensor processed event may be stored in one or more repositories, including a distributed ledger, without the underlying data being stored or made available to any other sensor, device and/or system.

In some embodiments, a sensor, device and/or system may be configured to retain and/or store data sets based on one or more location-based criteria, for example a geo fencing of a location. In this manner data can only be retained by one or more sensors, devices and/or systems when those sensors, devices and/or systems are active at certain locations. These can be further configured so as to constrain the time period during which such data may be retained, for example only during working hours, or conversely only when a PUM is sleeping.

The expression of privacy of data sets concerning a PUM and their environment is at least in part contextual, in that the context at least in part can determine access to and acceptance of information pertaining to a PUM, their environment and any events therein, can be implemented and enforced though the deployment of one or more tokens representing these data sets. This includes data sharing, which is typically dynamic, real time, and often pattern and/or event driven.

Tokens may, in some embodiments, be preconfigured or configurable, such that there may be standard tokens, representing for example, repeated events, occurrences, specifications and the like, which can be shared between multiple sensors, devices, systems and/or stakeholders, whereby each of these can contribute data to such a token and/or may provide configuration data sets through reference or embedding.

One aspect is the sequence of token creation, use and/or redemption, where for example a specific set of tokens in a specific order can form part of a pattern and/or pattern element and/or represent an event and/or event sequence. For example, the order of token exchange, communication and/or transfer between a set of sensors, devices and/or services can be independent of the order of events and/or events sequences represented by one of more token.

The combination of proximity, including having a person present at a PUM's environment, may determine, in whole or in part, the extent of data exchange between the environment, stakeholders, sensor devices and/or systems. In the example where a PUM is present, a token, sensor, device and/or system may be configured to restrict the distribution of some data sets, through for example their device acting as proxy, though for example an application and/or configuration, such that only certain specified stakeholders, devices and/or systems receive certain data sets. This expression of data privacy by a PUM can be subject to the HCP under which they are operating and/or such data that is made unavailable to the stakeholders, sensors, devices and/or systems, may be transferred to their digital twin.

In some embodiments, temporary relationships with third party devices, such as Alexa, Smart TV's, smart speaker and the like, can be established through the use of temporary tokens, which can be resolved by such device through, for example an intermediary, such as a cloud service, router, care hub, network device or other interpretation service, such that the device can, on a temporary basis be configured to provide data to other sensors, devices, systems and/or services in support of a PUM undergoing an event, for example the transition from one pattern to another. This may be the case, here the PUM enters an environment where they are not normally domiciled and/or where a stakeholder, such as a caretaker, enters an environment. Often such third-party devices may be configured to provide data that is supportive of the primary sensors data sets, for example, those generated by a PERS or other worn or carried device. This can include communication capabilities for communications with the PUM and/or other stakeholder, such as a care giver. For example, such data may confirm a situation, validate the date from a sensor and/or provide data that mitigates an event or action. Such data may provide contextual information that becomes part of an environment sensor array on a selective timed basis, for example such a device may be configured to listen for cough, fall or other care and wellness occurrence.

Token Issuance

In a care village there may be multiple tokens issuing authorities in any arrangement. For example, an issuing authority may have a domain, such as an organization, for example an aged care facility or the operator of a number of aged care facilities. In this example such an operator may issue tokens that are unique to the operations of that organization and/or have interoperability with token systems of other organizations. The determination of the scope of token operations a facility may support can be instantiated with the use of smart contracts for those issued tokens and public, private and shared distributed ledger arrangements. In some embodiments this may include the use of an exchange capability where tokens issued by an organization are exchanged for tokens issued by another organization and/or tokens that are recognized on a system wide basis.

In some embodiments one or more issuing services, operating as issuers, may be instantiated to provide one or more token generators with appropriate authority to create one or more tokens. In some embodiments such token generator may be a hardware device, comprising for example an FPGA or other programmable hardware element that can generate tokens based on one or more algorithm, such as for example a hash. In some circumstances where the token is representing a data set that is deemed private and/or secure, the token generator may communicate with the issuing service to apply one or more encryption technique to such token, so as the ensure the privacy and security of the data represented by the token. In some embodiments, this may include the token including sufficient token identification such that the token may be directed to an appropriate receiving sensor, device and/or service, whilst retaining the privacy and security of the data set represented by the token.

In some embodiments a token can be created by one sensor, device and/or system that can be interpreted by another sensor, device and/or system, providing a means for the exchange of data between the two sensors, devices and/or systems. Such token creating sensors, devices and/or system and token interpreting sensors, devices and/or systems may be located in the same physical or logical arrangements, where those arrangements can provide a further informing information set based on the relationships between the devices, tokens and/or issuing authorities. For example, time stamps, network locations, mac addresses, and other meta data may be supplied, in whole or in part as part of or in addition to the tokens exchanged between the sensors, devices and/or systems.

An embodiment may use different mechanisms to represent data as tokens. These mechanisms may include, for example, the token being an encrypted version of the data, the token being the address (encrypted or otherwise) of a storage location of the data in a data storage (local, centralized or distributed) system, or in a distributed ledger, the token being an index to the data in a data storage, the token being an identifier of the data in a distributed ledger or in a database management system (local, centralized or distributed), etc. Depending on the mechanism used to represent data as tokens, such as those instantiated in a token services module, there may be a variety of token issuing capabilities. For example, tokens of differing types and complexity may be issued by one or more sensors, devices and/or systems. In some embodiments sensors may issue tokens that represent an event or occurrence with the data of that event and/or occurrence held by the sensor. For example, a camera or other detector, using edge detection, may detect a change in the vertical alignment of a PUM, which may indicate a fall. In this example the sensor may issue a token representing the change in state of the PUM to, for example a service that monitors state, for example a care processing system. This token may then cause such a system to evaluate other sensor data, such as those carried or worn by a PUM, to ascertain whether this is a fall or whether the PUM sat down abruptly.

When the token is an encrypted version of the data, it may be issued by a sensor, device and/or system, by applying an encryption algorithm, such as AES, to the data. The device may also issue the token in cases where the token mechanism is an address or an index to the data in a data storage. In these cases, the data storage may be local or may be external and/or distributed. Similarly, in the case where the token is an identifier within a storage or database management system, such system may exist within the device or may be external to it.

In some embodiments, a token can be an address, an identifier or other reference to data stored in a storage system that is external to the device, such storage system may be a distributed file storage system, such as InterPlanetary File System (IPFS), where multiple devices, connected through a computer network, use a protocol to store data collaboratively and in a decentralized way.

When the token represents data stored in a distributed ledger, a device may include a local node of the distributed ledger and/or may be connected to a node of the distributed ledger. The device may use the distributed ledger node to request the issuing of the token by initiating a transaction within the distributed ledger that executes a smart contract, including issuing the token. This transaction can be validated by the distributed ledgers consensus mechanism, such that the smart contract is executed and, if successful, the token is returned to the device. This token may be the address of the data record in the distributed ledger or other representation of the data, the data ownership and other attributes within the distributed ledger. In some embodiments the validation of the requested transaction, the execution of the smart contract and/or the storing of the data can have an inherent cost, which must be paid by the requester. This cost may be translated into financial cost or may be abstract and exist only as a mechanism to control usage and access to resources within the distributed ledger.

Tokens, especially tokens based on a distributed ledger mechanism, may have a value that can be exchanged, aggregated, combined and/or used in financial or care service-related transactions.

In some embodiments, there may be types of token issuance, such as for example, open token systems, where token issuance is unlimited or closed token system where token issuance is limited, though in some embodiments this may be extensible. The choice of deployment strategies may be influenced by the distribution of the tokens, costs of issuance and the like.

In some embodiments, specific devices or classes thereof may have the capability to issue tokens, whereas other devices may only be able to receive and/or redeem them. This can include the situation where a device may only be able to issue a token that includes the identity of the device (which may incorporate time, location and other identifying characteristics), for example, a sensor deployed at a specific location for monitoring of a specific PUM. In some embodiments, this may be the only way such a sensor can propagate the data generated by such a sensor. In this case such a sensor may be able to receive and interpret a particular type of token, for example, a configuration token that includes data specific to that sensor or class thereof. Such a token may have identity information encoded and/or referenced such that the sensor will only accept such a token if the identity information is recognized as an authentic, authorized and validated source for such configuration information. This approach can be instantiated using standard authentication, authorization and access control techniques (AAA).

In another example, the sensor may delegate the token issuance to a service that is accessible, generally in a secure manner, to that sensor, such that processing overhead is removed from the sensor. In many circumstances this may include the sensor being hard wired and/or using a closed and/or secured communication system to such a service, such that the service can act as a proxy for the one or more sensor. For example, such hard wiring and/or closed communication system may be a closed system with no external access to the sensor other than through the service. Such a service may also accept, interpret and consequently configure a sensor controlled by that service upon receipt of a configuration token. For example, a care hub may act as such a service, with each of the sensors operating in an environment hard wired and/or connected using a closed secured communications system, such as for example, using hardware addressing using MAC addresses or other suitable hardening techniques.

In some embodiments any sensor, device, system and/or stakeholder may issue tokens, either directly or through a proxy, for example a token issuing system. These tokens may form localized arrangements, whereby the tokens can only be issued and redeemed by a closed set of authorized and authenticated identities. For example, this may be a family group, a PUM and their caretaker, a PUM and medical professionals and the like. Such localization may be based on physical and/or logical determinations. For example, a PUM may localize their group to themselves and their digital twin.

Distributed Ledger Configurations

In some embodiments, a distributed ledger may include and/or be connected to at least one protected processing environment. Such an arrangement can support both fungible and non-fungible tokens. Such distributed ledgers may be public or private.

In some embodiments, querying the DL may involve receiving a token, which for example represents an event and/or pattern, or part thereof, such that the recordation of the event or pattern able to be relied upon, without disclosing the underlying data.

In some embodiments there may be local ledger nodes, for example those operated by a PUM, a facility, an insurance or other service and/or product provider and the like. In some embodiments tokens may have specifications and/or the smart contracts for those tokens may include specifications that are proximity based, in that certain conditions for proximity of the tokens can be enforced.

In some embodiments a PUM in an environment under monitoring, may have data generated by sensors processed by a care processing system using a protected processing environment, where that environment communicates with one or more digital twins in a secure manner, such that the data generated by the sensors, processed by the care processing system and communicated and acted upon by the one or more digital twins is always secured. For example, the digital twins may incorporate digital twins of the sensors monitoring the PUM and their environment and care processing systems, such that the data supplied by the sensors monitoring the physical PUM and environment are represented in the digital twin. the Relationship between a protected processing environment and at least one DL In some embodiments, the data from the sensors may only be available to specific stakeholders in specific circumstances, whereas for the digital twin to represent the PUM and their environment, the sensors data may need to be available. The sue of protected processing environments to connect and communicate between the sensors and care processing of the physical PUM and their environment and the digital twins representing these entities ensures the security of the data is maintained.

Figure 21:
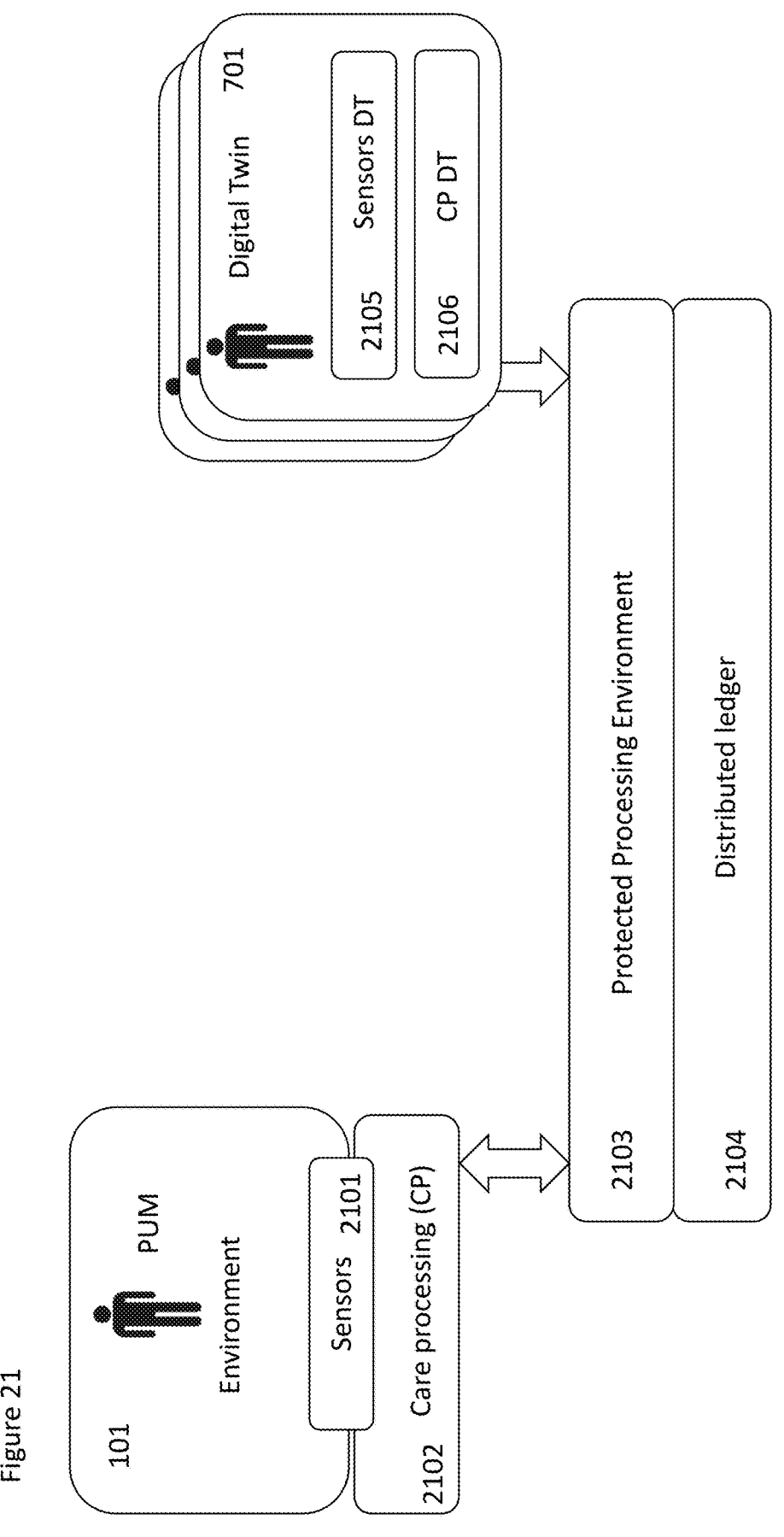
FIG. 21 illustrates a PUM in a monitored environment.

FIG. 21 illustrates a PUM in a monitored environment (101), in which sensors (2101) are undertaking monitoring and providing data to a care processing system (2102). In this example the care processing system is providing such data through a protected processing environment to one or more digital twins (701) comprising at least in part digital twin representations of sensors (2105) and care processing (2106) so as to represent the physical equivalents. For example, the protected processing environment may then store the data, processing and other meta data to a distributed ledger. This can include the use of tokens.

Token Interactions

In some embodiments, a sensor may generate a token representing one or more data set. For example, this can be an event, detected by that sensor and may include feature sets that such a sensor can recognize. The creation of such an event may include the sensor interacting with either an on device and/or networked issuing capability in a secure manner, such that the token includes data that can only be created by such a sensor with such an issuing capability, for example a server, router, switch, care hub or other device and/or service capable of creating such a token, at least at one location, and within a specific time range.

In many circumstances a token can be generated by at least one event, for example this may include a visit by the caretaker/family member of other stakeholder, a device activated event, a sensor activated event and the like.

Tokenized information can inform one or more stakeholders without the provision of the underlying sensitive PUM care and wellness information. The distribution of the information represented by the tokens can be controlled by the tokens themselves, in that the identity of the stakeholder, including their role in a care village, can be determine to what degree the token data is made available. The data distribution may also be controlled by a cloud or other service which may extract data from a token, using relevant credentials, and/or may convert the token to another token for a specific stakeholder. The service can directly inform the stakeholder of the data of the token. The service may provide such data either through reference or embedding in, for example, further tokens.

The use of a service that can accept, redeem and/or issue tokens can provide a set of stakeholders with a form of mediated data exchange that enables each of the stakeholders to access that data that is pertinent to a situation and context without undermining the privacy of those stakeholders and/or the service. This can be in form of a token exchange where, for example, a token with multiple data sets each with specified credentials required to access such data could be separated into individual tokens representing a single set of data and associated credential requirements. For example, if a token comprises a number of data sets, for example those created by one or more sensor sets, such data sets may be distributed to specific stakeholders, where each stakeholder has access to that data for their specific purpose.

Sensors, devices and/or systems can be represented by one or more token and may interact with other system elements through these tokens. Such tokens can represent data from such a sensor, device and/or systems, commands, configurations and/or other specifications that can, for example, manage, instruct, and/or vary the operations of those sensors, devices and/or systems.

In some embodiments a sensor, device and/or system may only be able to accept specific tokens, representing a set of specifications, where the identity of the token provider is part of the token and the one or more data sets represented by the token are codified in such a manner that only a specific sensor, device and/or system and/or class of sensor, device and/or system can interpret the one or more data sets.

In some embodiments, a device and a stakeholder may have a static or dynamic relationship. For example, a stakeholder may have a smart phone which they own and control and/or another device, such as a sensor, that can create data about them. The use of tokens to represent these relationships, such that the separation of ownership, use, data creation and/or data distribution may be represented by one or more token.

Token access and use may be managed by multi factor authentication and/or one or more biometrics.

Tokens and Rights

The issuing of a token, for example one created as the outcome of an event, pattern and/or other occurrence, may be instantiated, and the storage of that token may be constrained to a device and/or a repository that is securely managed by or on behalf of that sensor, device and/or system. The token distribution, including the rights required to access the at least one data set represented by the token, may be subject to further tokenization of those rights.

The configuration of one or more sensor, device and/or system may include one or more sets of specifications that in whole or on part determine the issuance of tokens by and for that sensor, device and/or system, including the identity of the sensor, device and/or system, the distribution of that token and any processing of that token.

For example, a set of devices may create a set of tokens based on, for example an operating pattern, representation of that pattern. This may be the case when the pattern is quiescent, in that the care state of the PUM is unchanged. The recordation of this data may be used, for example, by one or more digital twins, where this data and the data from other PUMs can be evaluated and compared so as to identify characteristics that may indicate a change in the care state of one or more PUM.

In some embodiments, session tokens, that is tokens created for a specific time period at a specific location and/or potentially involving specific stakeholders, may be created. For example, there may be specifications for such a token, where the presence of one or more stakeholders is detected at a location, for example by an edge sensor, within a certain time period and/or at a location. This token data can be used to configure one or more sensors to generate one or more data sets that represent the validation and/or verification of the presence of the specific stakeholders and/or the confirmation of the location, such that the occurrences, including events, actions, responses and/or activities, occurring during the specified time period result in the issuance of one or more session tokens. This can involve access to data, configuration of one or more sensors, devices and/or systems, other sensors, devices and/or systems, one or more processing systems and/or one or more locations, including care and wellness services and capabilities in support of the care and wellness of the PUM.

For example, a PUM may only be able to receive a specific prescription, procedure and/or other care and wellness resource, when, for example, they are at a specific location and/or in proximity to or in contact with, for example over a secure communication system, a specific stakeholder within a specified time period. Such proximity or contact may be determined through the colocation of one or more devices representing such PUM, Stakeholder and/or location, including sensors, devices, systems and/or services.

For example, one or more session token can include specifications, for example rights, authorizations, programmatic materials, for example those associated with smart contracts and the like. In some embodiments, such specifications can enable the execution of the actions, events and/or responses by one or more stakeholder, including roles for example those roles with, multiple stakeholders, that may have one or more-time constraints, limits and/or thresholds. In some embodiments sets of session tokens may be required to initiate an action, event and/or response, for example where multiple stakeholders are required to be present or in contact and/or provide such a session token. For example, this may be the case where a significant financial, care and wellness and/or legal action, event or response to be undertaken.

Figure 9:
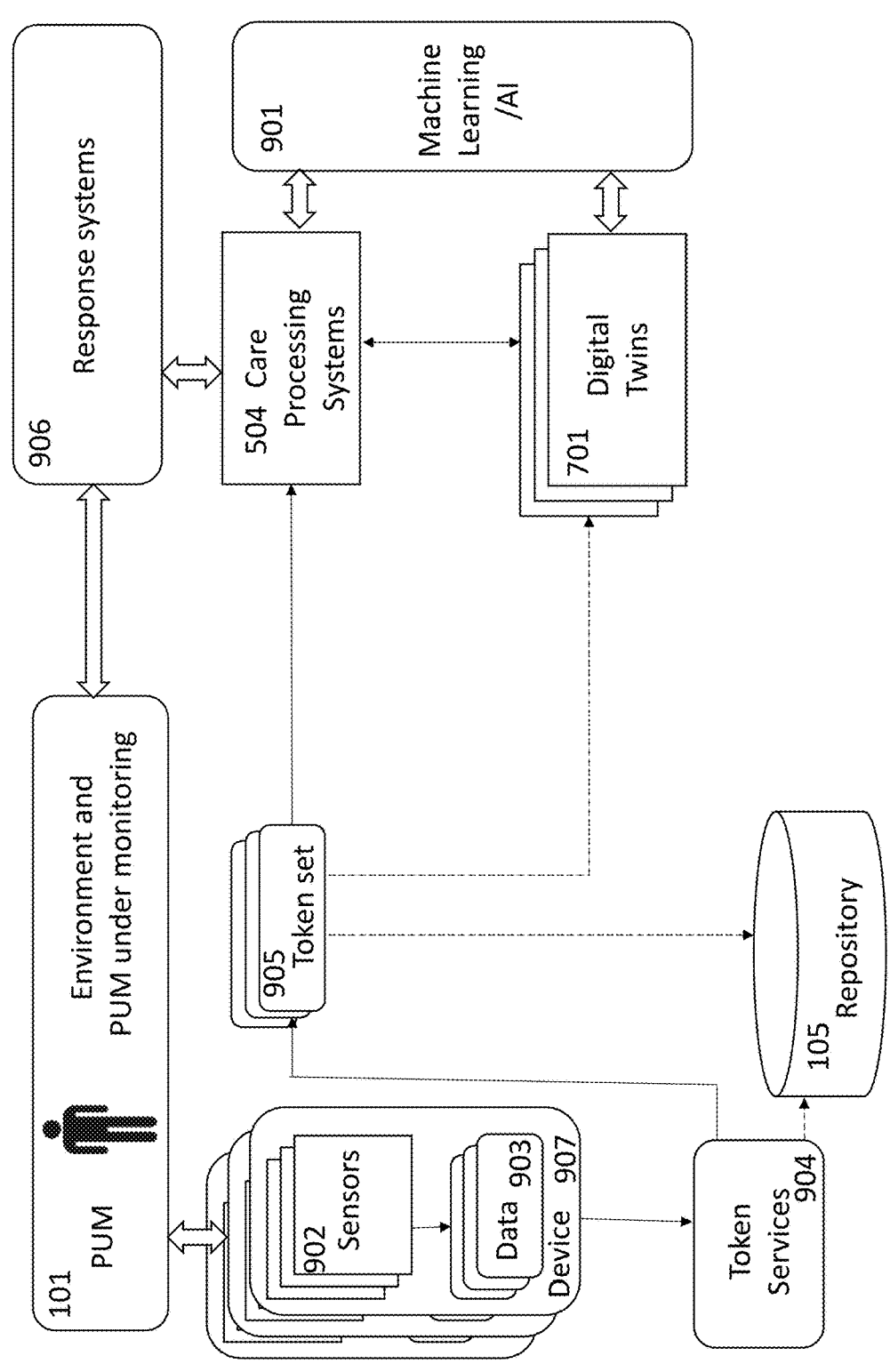
FIG. 9 illustrates a PUM in a monitored.

FIG. 9 illustrates a PUM in a monitored environment (101) where one or more devices (907) comprising at least in part, sensors (902) generating data (903), which is then securely communicated to token services (904). In this example, token services generate tokens (905) which are communicated to care processing systems (504), which may invoke machine learning and AI modules (901) and/or digital twins (701) in any arrangement. Care processing systems can invoke and instruct response systems (906), that may then provide one or more responses to PUM and/or other stakeholders for environment under monitoring (101).

A token may represent a set of specifications, including those expressing rights, that have differing actions and/or outcomes based on the context of the token. For example, in a situation that is not designated as a care emergency a token can enable specifications set (A) to be available to a set of devices, sensors, stakeholders, system elements and the like. However, in a situation designated as a care emergency such a token can enable specifications set (B), where for example specification set (A) is a subset of specification set (B), such that specification set (B) provides additional specified rights to one or more specified stakeholder and/or third party. In some embodiments such a third party may have their own token set.

The determination of a situation, such as one where an emergency or other care event is occurring, can be represented by the at least one pattern operating at that time. Such patterns may include the provisioning and use of tokens in any arrangement. For example, a pattern may include tokens that are retained by sensors, devices, system and/or stakeholder and the like that are part of such a pattern. The pattern may also include other tokens that can be made available to specific of the sensors, devices, systems and/or stakeholders and the like that are part of that pattern. In this manner, for example, a device may receive a token that when processed by the device changes the configuration of that device, such that additional data and/or control of that device is passed to other system elements, stakeholders, devices and/or sensors.

For example, in a situation that is at least in part represented by one or more pattern, stakeholder A having possession and control, either through reference or embedding, of token A1 may provide data set A1.1, being in whole or in part a data set of token A1, to one or more other stakeholder, sensor, device and/or system. In a second example situation, which may be represented by the same or differing pattern, such a token A1 may provide a second data set, A1.2, to the same or differing stakeholders, devices and sensors and/or systems in any arrangement. The data sets A1.1, A1.2 and any others managed by that token, can be in any arrangement, including for example, subsets, supersets, hierarchical, taxonomic and the like.

There may also be location-based determinates that are, for example, invoked by a pattern and/or other sensors, devices and/or system elements. For example, if a stakeholder C is present at a location with token C, then token A may provide data set A1.3.

The relationships between tokens can be dynamic and/or predetermined. Tokens can also have differing identities, such as classes, where a token of a type of class may provide all the data it is capable of providing to a device, sensor, system and/or stakeholder that has a token of the relevant type to enable such an occurrence.

In some embodiments, sets of tokens may need to be available to one or more stakeholder, sensor, device and/or system for data to be made available, events, outcomes and responses and/or other actions to occur. This can include a token which has, for example, a number of data sets, each of which can be separated at least in part and using an authorized issuing service, such as a token services module. For example, such a service may receive a multi segment token comprising multiple data sets and based on specifications, may then disaggregate such token into separate tokens for distribution to differing stakeholders, devices, sensors and/or systems.

For example, where multi segment token A comprises, data set A1, and A1.1 is a subset of set A1 and token A also comprises data set A1.2, where A1.2 is a subset of data set A1 and A1.3 id a further subset and the like.

Token set H may comprise (J, K, L, M) where each of these tokens incorporates part of the overall specifications represented by Token H.

In some embodiments, establishing trust between entities, be they stakeholders, systems, devices or other care village identities can be instantiated through the use of tokens. For example, two devices may instance a token and pass this token to each other, such that the relationship between the devices is signified as trusted. This can be embodied through the use of PKI or other cryptographic techniques. Another example can be the proximity of one token, for example a token in a smart phone with a proximity application, which on detecting another device with an appropriate token may determine that data from that device can be trusted.

This can also apply to stakeholders who may, upon verifying a data set provided by a device can designate that device as trusted, and as such the data from that device can be relied upon, within the specifications of that arrangement.

The inverse is also the case where for example, a PUM may have many data sources offered to them, for example advertising a product or service or conveying data from a certain perspective, where these devices have no trust relationship with the PUM and their device.

Any stakeholder may establish a trust relationship with their devices, for example using biometrics and/or multi factor authentication. The care village may provide tokens that incorporate a unique identity for that device and/or stakeholder, enabling participation in the care village.

Tokens and Identity

Token may represent one or more identity in a care village. This can include any system element in any granularity and/or any stakeholder in any arrangement. In some embodiments, the identity of stakeholders, including individuals and organizations, may be based on multi factor authentication, such as biometrics, devices, tokens and the like in any arrangement.

Each PUM and their domiciled environment can have a unique identifier for their participation in the care village, as does other stakeholders of that village. There may be multiple identity schemas used in such arrangements, such that each identity can be represented by at least one token.

In some embodiments, a PUM, or an authorized proxy thereof, may include an issuing capability, so as to create tokens that can be attached, bound, referenced, embedded or in other manners form part of a set of tokenized data that can represent an event, action, situation, response, condition, transaction, temporal period or any other data set in the care village.

In some embodiments, identity of a stakeholder, sensor, device and/or service or other system element may involve multiple factors, such as biometrics and/or other authentications from one or more stakeholder, device specific UID and/or other identifiers, service identities, including end points and/or other registered authenticated service identifiers represented by one or more token. These identity factors may then be combined in any arrangement with other specifications, such as time, location, coincident and concurrent system elements (including other stakeholders and/or devices) and the like and be represented by one or more tokens.

In many cases proximity may be a determining or contributing factor in the verification and authentication of an identity, for example through the use of a token that can only be issued at a specific location or in proximity to a specific one or more devices, with a data set that can only be interpreted by specific devices. For example, this can include session tokens.

In some embodiments, certain identity specific information may form part of all tokens issued, communicated and/or redeemed within a system. For example, if there is a particular realm or domain, for example an aged care facility, only those tokens that include an appropriate identifier will be accepted by sensors, devices, systems and/or stakeholders that comprise such a realm or domain.

For example, a stakeholder who is a representative of a service provider (SP) may be the recipient of data created by one or more sensor. In this example such a SP sends a request to a data provider (DP), for example a sensor, device, system and/or smart contract representing such, that is be monitoring a PUM where the data of the PUM is generated and/or stored, by reference or embedding. The sensor, device, system and/or smart contact of the PUM, depending on the identity and credentials of the service provider may opt to provide or deny, in whole or in part, the data requested by the service provider. This can be dynamic, in that the election to provide or deny the data may be determined by the PUM, their device and/or a proxy based on the context and/or the data requested. This can include decision processing that is based on specifications and/or on the interactions of the PUM. In this manner the PUM can have elective control of the data instantiated by the sensors, devices, systems and/or smart contracts deployed in monitoring them, including such data generated by any devices under the control of the PUM.

In some embodiments, a data provider may have preconfigured end points for the data, for example a designated care hub, care processing system and/or other sensors, device and/or systems, including for example smart contracts. This can include a service provider, however the data provider configuration may determine, for example that the service provider, upon receiving a token representing the data may be able to determine that the token represents the data, for example an event and/or action or set thereof, though without having access to the underlying data of the data provider. This can ensure that only data that is relevant to the service provider is accessible to them and can ensure the privacy of the data provider, for example a PUM, whilst supporting the service provider operations.

In some embodiments, a data provider, for example a sensor, device, system and/or smart contract, may sign a message from a service provider that is requesting data from the data provider. This can be in the form of a signed token, which may include, for example configuration data confirming the operations of such sensor, device and/or system without revealing the data that has been generated by those operations. This can include references to such data, for example stored in an elastic repository, where for example care processing or other systems may determine access rights for that data. For example, a service provider can send a signed token provided by data provider to one or more other systems, including for example, care processing systems, where an authentication module may operate to support the availability of the token data in pursuit of the relevant service provision of the service provider. Such an approach may be instantiated using session tokens, which represents the time, location, identity and other salient data as to the occurrences that generated the data represented by the token generated by the data provider.

In some embodiments, a token service may include a token identity service, which, based on the identity of the token, can undertake one or more processing operations. This can include distribution of these tokens to appropriate end points as determined by the token identity information. For example, if a token from a sensor set includes the identity of that sensor as the source, for example a stakeholder device, a token service, potentially in collaborations with a care hub, care processing or other system, may determine one or more end points for that token. In some embodiments, this can include asymmetric encryption, such as public key encryption or other appropriate key schema.

In some embodiments, various types of tokens, for example other tokens as illustrated in FIG. 3 may be used throughout the care village. These can include, for example context tokens and care tokens, however various other token types may be instantiated by the care village as required.

A context token represents a context within the care village that has previously existed, is in existence at the current time or is predicted to exist in the future.

A context token can be evaluated by a receiving party end point to establish events, actions and/or other occurrences as determined by the end point which in whole or in part represent a meaning through this interpretation by the receiving party. In some embodiments, a first party receives a context token, evaluates the token identity and/or data to create an interpretation including in the form of a further token, which is then dispatched to second party. In this manner the second party receives only the data determined by the first party, which may confirm an event, alert and/or occurrence, without disclosing the underlying data to the second party.

In some embodiments a first party receives a token for which they do not have appropriate rights or keys to access the token data, and as such the token is passed to a service, such as a token service, care hub and/or care processing system which has sufficient rights to evaluate the token and then returns a further token to the first party that can be evaluated by that party and includes the relevant data for that party.

Care tokens can represent a care and/or wellness situation, such as for example a completed care condition or a care transaction. In some embodiments a care token can represent the completion of a care event, for example completing a course of medications, physical or other therapy and the like. A care token may also represent a care condition or combination thereof, for example a prescription, request for product and/or service and the like. This can include the identity of the PUM and/or other sensors, devices and/or systems that are proxies for the PUM to, in part, provide accurate confirmation of the identity of the care token holder. For example, this may in the form of a bearer token which is biometrically and/or otherwise bound to the holder of the token, for example a PUM. In some embodiments care tokens may be transacted in a care village marketplace.

There may be classes of tokens that can be combined in any arrangement. One form of embodiment may be the use of set theory for token combination and manipulation.

In some embodiments, identity information may be stored in at least one distributed ledger and/or proxy thereof. In this manner an immutable record of an identity may be established, as can be the various HCP, patterns, events and other data that are fragments of that identity.

Token Applications

In some embodiments, an event and/or pattern detection in an environment may generate one or more token, which can be passed to one or more device, in that environment and/or remote to the environment as well as to relevant stakeholders who are involved in the care and wellness of the PUM in that environment.

These tokens may include multiple data sets and, in some embodiments, can include time or other specifications that can be accessed in an ordered and prioritized manner by a sensor, device, system and/or stakeholders that have received these tokens.

For example, a care giver may receive a token that alerts them to an event and advises them of a triage operation being undertaken at the environment, for example a suspected fall is being evaluated. Once the evaluation is undertaken the token may release further details held by that token, either through reference or embedding, of the event, the person involved and the subsequent actions to resolve the situation. In this manner a series of states may be created, which may be represented by a set of tokens, each set being part of a pattern to be deployed on matching the detected data patterns on and from a PUM.

In some embodiments, tokens may have data payloads that require multiple devices to collaborate in a specified manner to access that data. For example, a first device generates one or more token, and first device sends one or more token to second device. The second device receives one or more token, and the second device is configured to interpret a subset of the token data. Such a second device may request and/or be configured and/or instructed to contact the first and/or a third device so as to carry out the at least one operation based on the configured access to data in the token.

In this manner a third device may act to instruct and/or configure the second device, without the second device having any access to data held by the one or more tokens.

A token or set thereof can represent event(s), action(s), response(s), pattern(s) and/or other occurrences, which when passed to an appropriate device and/or system, such a device and/or system may employ one or more processing units on that data to verify the event(s), action(s), response(s) and/or pattern(s). This can be in the form of one or more token which represents such a verification, however the one or more token may not reveal the data of and for that verification.

In some embodiments, gamification "token sets" can be used to represent positive/negative care and wellness activities, for example, including user event sequence tokens, including one or more tokens representing patterns. For example, a pattern that includes an exercise event sequence, may have a token representing that part of the pattern that is passed to a gamification engine which displays the benefits and metrics for such exercise in a care and wellness beneficial manner. The same approach can be used for activities that are likely to produce negative health outcomes, such as for example siting of extended periods without movement. The representation of these care and wellness metrics is well suited to gamification and may use, for example instantiations that employ unreal engine or unity as the game engine, however the use of tokens as both the data provision mechanism and in some examples as the game incentive mechanism can provide significant user advantages, including selective accessibility of those data sets in the context of PUM privacy.

Tokens and Environment Sensing

In some embodiments, one or more tokens can be used for inter and intra sensor, device and/or system communications. These communications may be in the form of tokens which represent a specific data set, that is a representation of an event, action, response, sensor detection, pattern and/or the like such that the source of such data is recognizable by the receiving party. This could be an identity that provides sufficient information so as to identify the originator of the token and the representation of an event, action, pattern, detection or other sensor state change.

In this manner the data may be transferred from a sensor, device, system or other entity to another without compromising the privacy of the source and yet conveying sufficient data for appropriate actions, processing, configuration or other activity to be undertaken.

The arrangement of such networks of sensors, devices and/or systems may be pre-configured and/or dynamically instantiated. This is particularly important in the case of a severe care situation where the data transfer from one set of sensors, devices and/or systems to another may be crucial for the well-being of the PUM.

Tokens may be communicated between sensors, devices, systems and/or other system elements and can represent data sets that are held or managed within or by those sensors, devices, systems and/or other system elements and/or in their proxies such as repositories, including distributed ledgers. The tokens may then cause or invoke certain activities to be undertaken by such, sensors, devices, systems and/or system other elements.

In some embodiments a set of sensors may detect a change in the state of the environment, including a PUM, that is being monitored, each of which may then generate, for example, a state change token, which can represent the specific change that the sensor has detected. Representations of these changes may be held in one or more repository, where the state change can form part of a pattern specification, pattern element or other organization of the data. There may be sets of conditions, that when satisfied, cause further tokens to be generated which can then be communicated to the one or more sensors, devices, systems and other elements. Such tokens may cause these to change their configuration, through for example, the token representing an identity and/or value which the sensor, device, system and other element may then interpret as specifications, either embedded or by reference.

One aspect of the system is the use of sensors to monitor a PUM in an environment, often their domicile. These sensors can be configured to provide data in a format, such as a token, that can be evaluated, in part or in whole, by one or more processor so as to establish the relationship of the token with a pattern of behavior for that PUM. This can be achieved such that the sensor can incorporate programmatic processing to convert, for example, raw sensor data into a form that can be evaluated within a pattern, and yet retain the privacy of the PUM. For example, in the case of a camera, the arrival of a PUM in an area, for example a living room and their sitting down, may be represented as a token and as a behavior that forms part of a pattern element without the image capture of the PUM being transferred to any repository configured by the pattern monitoring or any other system element.

In some embodiments, this image data may be retained by the sensor or its proxy, for example a secure digital twin, for a period of time, in case the PUM undergoes a wellness event to which such imagery would be informing, otherwise the imagery is deleted. In this manner the pattern of the PUM behavior is retained as is the privacy of the PUM.

Tokens can be used for configuration and/or data. In some embodiments this can be in the form of separate token types and/or as multipart tokens which include both configuration specifications and data.

Tokens may represent one or more events including sets thereof, which can be communicated to other system elements, including for example care processing systems, other sensors, stakeholder devices and/or one or more authorized digital twins and the like.

In this manner the data of the event and the token representing the event can be separated, such that patterns or other system elements may utilize the tokens and the event state they represent without accessing the underlying data and thus preserving the privacy of the PUM and/or other stakeholders.

This enables the system to verify that certain events occurred whilst retaining the privacy of the PUM and/or other stakeholders. In some embodiments there may be multi-layer tokens, where an issuing service generates a multi-layer token at point of origin, for example in a device containing one or more sensor, a network device connecting a set of sensors, for example a care hub, and/or another authorized proxy for the one or more sensors. Such a multipart token may include a framework which is in part populated by data generated by the one or more sensor, and as this multilayer token traverses the system, further data may be added to the token framework. This can also include evolution of the populated portions of the token by such system elements which can then result in additional data being populated into the token and/or such data being used for one or more other system operations.

In some embodiment, tokens may be organized into, for example, ontologies, taxonomies or other arrangements. For example, there may be a hierarchy of tokens that can be issued by one or more sensors, devices and/or systems, where for example such hierarchy is based on severity of the sensed state, as determine by the sensor, device and/or system in any arrangement. A further example can be the arrangement of tokens for the configuration of one or more sensors, devices and/or sensors, such that varying degrees of configuration, such as fidelity or granularity are arranged in a hierarchical manner of tokens.

This can include the use of preformatted tokens based for example on types, ontologies and/or taxonomies, such that a sensor, device and/or system may have such tokens available, for example from a local or remote repository. This can be beneficial where battery power or other critical capabilities are constrained. There may also be preformatted tokens that are representing complex relationships between a set of sensors, such as those of a multi-dimensional feature set, where for example, if a set of thresholds and/or relationships are reached or exceeded one or more preformatted token may be issued by a service, such as a care processing service, representing a type of event, for example a fall. Such a token set may be communicated to the appropriate stakeholders, in place of the potentially large number of individual state change tokens from a set of sensors, devices and/or systems.

In some embodiments patterns and/or pattern elements can have tokens that represent one or more states of that pattern and/or pattern element, for example, quiescent tokens, state change tokens, sensor status tokens, sensor configuration tokens and/or tokens representing one or more events, actions and/or responses. For example, a PUM retiring for sleep at night may have a token presenting that pattern and/or pattern element, which can inform a care processing system of that state. Such an approach can ensure that the underlying data of that PUM is not revealed to a care processing or other monitoring system and yet such systems are reliably informed as to the state of the PUM. In some embodiments, one or more sensors, devices and/or systems may maintain the data sets they have sensed, for example in one or more elastic repositories. In some embodiments, on issuing a token, directly or indirectly, a sensor, device and/or system may continue to sense an environment and store the sensed data in an elastic repository, in the event that such data can be evaluated by, for example, a care processing system.

The use of tokens to represent one or more sets of patterns and/or pattern elements without revealing underlying data except, where there is a critical wellness or care need, such as an case of emergency, enables an effective monitoring capability whilst ensuring the privacy of a PUM or other stakeholders.

In some embodiments a processing system, for example a care processing system, can evaluate state variations of a multi-dimensional feature set through, for example, comparisons of sets of dimensions. This can include evaluation of data sets comprising such dimensions, which can be invoked through one or more token having been issued and/or processed. For example, if a sensor, device and/or system issues a token representing a change in state of that sensor, this may initiate a processing system such as a care processing system to evaluate the dimensions of a multi-dimensional feature set to which the data from that sensor, device and/or system contributes. This may include evaluation of sets of dimensions that are related to the dimension to which such data is a part.

Such evaluations may, through interpretation of feature set data, represent change in a care and wellness state, expressed as patterns of behaviors. In some embodiments this can include static and dynamic analytics of multi-dimensional feature sets to create quantized interpretations, including those involving machine learning and AI techniques. These interpretations may not necessarily be deterministic and may be based on fuzzy logic or other approximation techniques.

Patterns, Pattern Elements and Tokens

One advantage of the use of tokens is the ability for them to represent arbitrarily complex data sets, including structured and unstructured data This can include the representation of patterns and/or pattern elements whereby a token can represent pattern and/or pattern element, including the state of a pattern or pattern element, for example the quiescent state of a pattern of a PUM in the context of an HCP.

In some embodiments, a token, representing a pattern may be passed to a digital twin, where that digital twin may be receiving multiple tokens representing similar or same patterns of multiple PUM operating in a specific HCP. This enables a digital twin enabled machine learning system to undertake analysis of multiple data sets without compromising the privacy of a particular PUM.

Token may represent behavior sets, which may be pattern elements, including those representing transitions from one pattern element state to another. In some embodiments, these tokens may be of a specific class, for example, state change tokens, which can represent the change from, for example a quiescent state to an activated care and wellness state. These may be further organized within specific HCP, such that for example, if the HCP is a memory deterioration HCP, then the state change tokens may be instantiated when there is a change in the memory capabilities of the PUM that exceeds one or more thresholds, for example those of a multi-dimensional feature set. These tokens, when representing a pattern and/or pattern element quiescent state can be accumulated and used, for example, in metrics for a set of PUM to establish prediction of if and when a transition state, also represented by a token, is likely to occur.

Different projections from single token to multiple stakeholders—focus by Stakeholder type, e.g., comfort/wellness or risk One aspect of the system is the combinations of tokens that in aggregate create a provenance as to the events, actions, responses, data, stakeholder, timing, pattern elements, patterns and/or other system elements. For example, a token from a sensor, processed by a care of other processing system that has a known relationship with that token at a time that is consistent for both the sensor and processing may form part of a pattern that is operating as part of an HCP for a PUM. This data may be used to then verify or validate the actions of one or more stakeholders who were in the presence of the sensor at the time that the sensor provided the data and the care or other processing operated on the data as part of the patterns.

Further types of provenances of all aspects of the system including the sensors as originators of data, actions, events, patterns, transformations and other static and dynamic elements can be expressed with varying degrees of veracity.

In some embodiments a set of actions and/or events involving a stakeholder, for example a PUM, may be represented as a set of tokens. For example, if a PUM has a particular set of actions, for example upon waking they undertake a routine of exercise, breakfast, bathroom use and reading for a consistent period of time, then this set of data may be represented by at least one token. In this manner there may be significant efficiency gains in the disposition of data regarding that PUM, including their privacy.

There may be arbitrarily complex combinatorial possibilities for sets of tokens, where at least one token set may be combined with another to form a new set that for example, represents a behavior that is, at least in part common across a number of PUM within an HCP and/or patterns thereof. A set of tokens may represent a certification of a particular behavior, treatment, actions, events or other combination that is compliant to one or more specifications, for example those of a pattern.

Token Transactions

In some embodiments tokens may be used as the medium for communications, including transactions between multiple parties, including sensors, devices, stakeholders and/or systems. There may be types of tokens that are specific to differing transaction types, for example, one type of token may be used for transactions that have an end monetary value or a different type for care and wellness specific data sets and/or another type for sensor, device and/or system data that is informational in nature.

In some embodiments this can include digital currency tokens, for example those available in a wider context such as bitcoin and the like and/or those that are specific to a particular realm, such as an aged care facility, an insurance operated system, a care village, local neighborhood and the like. This can include various types of value representation including fiat and sovereign currency, pseudo currency, loyalty or other reward schemes, for example a neighbor may accrue "care points", represented as tokens for undertaking activities that support a PUM, and the like.

There can be markets for such tokens set up and operating at any scale within a care village, health facility, neighborhood, stakeholder arrangement and/or any other grouping where the exchange of tokens can be transacted.

In some embodiments, data sets may be employed that are representations of proofs of actions, events, timing, behavior, interactions and the like, for example this can include events, sequences of events, satisfaction of specifications and the like. This may include the use of pre and post conditions for such specifications, which can be, in whole or in part represented by tokens.

Tokens may be aggregated into sets of tokens representing, for example, multiple events, proofs, values and the like.

In some embodiments, a market for tokens may include, for example a matching system that matches a bid or request token to an offer token. This can include probability-based matching, fuzzy logic, constraint analysis and may include the use of smart contracts and/or other programmatic elements. For example, a token can represent, an offer (an offer by a stakeholder that includes specifications that are to be satisfied), a bid (a bid to meet the specifications, in whole or in part, of an offer). This can include multipart tokens that have increments of satisfaction, whereby as each specification is satisfied, further detail, which can be informational and/or transactional is revealed. These multipart tokens can form a type of triage whereby multiple bids are initially accepted and each of these receives a further specification for satisfaction until a relevant bid is accepted. In some embodiments a token matching service may be invoked to undertake this processing. In another embodiment, this may be undertaken in the form of multi part tokens by the stakeholders' devices. In the situation where this occurs between, for example two or more sensors, such multipart tokens may comprise data and configuration specifications.

Figure 14:
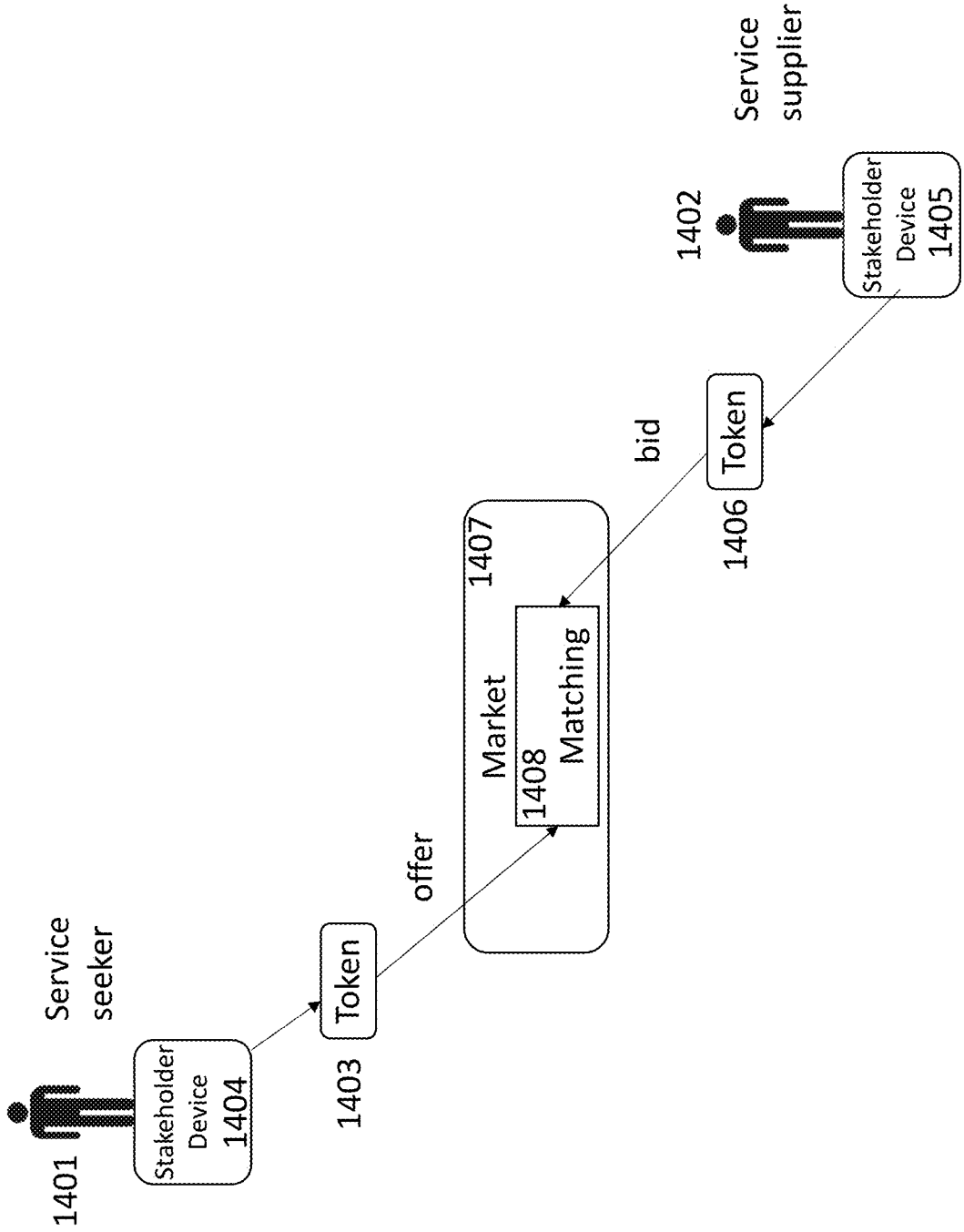
FIG. 14 illustrates a simplified example of a market.

FIG. 14 illustrates a simplified example of a market where a stakeholder seeking a product and/or service (1401) can, using a suitably capable device (1404), create one or more tokens (1403) representing their requirements which is communicated to a marketplace (1407) configured to accept such tokens. In this example a second stakeholder who is a supplier of a product or service (1402), can using a similarly capable device (1405) create one or more tokens (1406) offering such services, which can be communicated to a marketplace. In this example the marketplace (1407), comprises, at least in part, a matching module configured to match requested services and/or products to offered services and/or products that match the requirements.

Within the overall system, any of the system flows, events, transactions, processes, requests and the like can be represented by tokens. These tokens may be exchanged for other tokens, individually and in aggregate in any arrangement, for example is a token forms part of an event sequence (e.g., a task flow etc.), and the token may represent the complete sequence or a part thereof, the token can be exchanged and/or converted into, for example, Value (such as a fiat, digital and/or sovereign currency or other accepted value), one or more representations of verification, validation, certification or other message, an event, action and/or trigger and other tokens/message.

In some embodiments, Tokens can be typed and may be part of a classification schema, where such schema can have conditions and specifications governing the operations of such a schema in at least one context.

A care village marketplace can incorporate any and all stakeholders and their devices and tokens in any arrangement. The marketplace can require that any entity that interacts with the marketplace has a valid unique identity for the care village. In such an embodiment, the care village may include verification of the settlement of any obligations, bids and offers or other transactions, enabling a verifiable and authenticated audit trail for those transactional activities.

Figure 15:
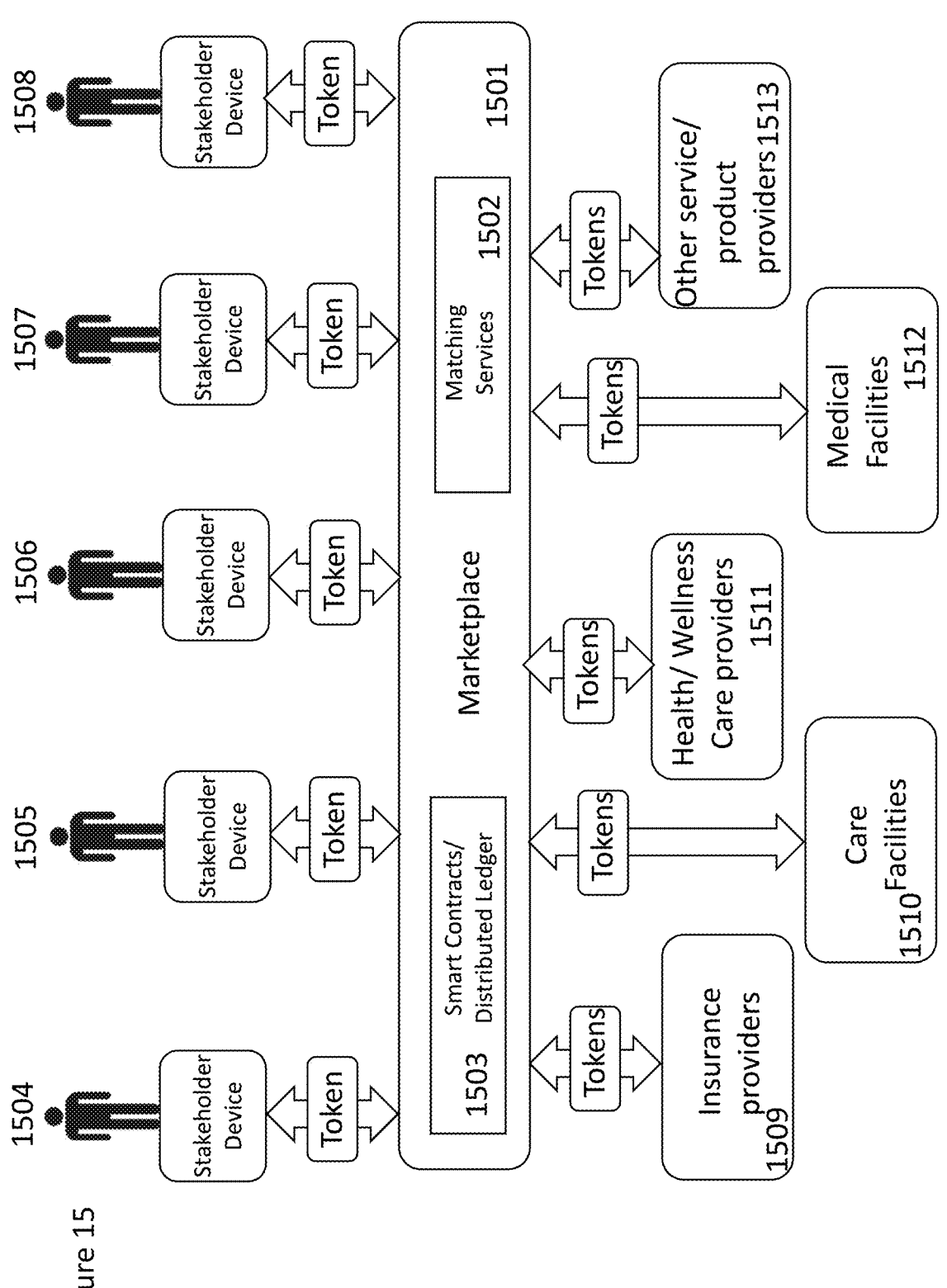
FIG. 15 illustrates an example marketplace.

FIG. 15 illustrates an example marketplace (1501), which in part comprises matching services (1502) and one or more smart contract and distributed ledger arrangements (1503). In this example, one or more stakeholders (1504 . . . 1508) through their suitably configured devices create one or more tokens which are communicated to the marketplace. These tokens may represent data of any type, for example request for products, services and like. Such requests may be satisfied, in whole or in part, by one or more suppliers of products and/or services, such as for example, insurance providers (1509), care facilities (1510), Health and/or wellness care providers (1511), medical facilities (1512) and/or other service and/or product providers (1513). In this illustrated example, the marketplace (1501) may use matching services (1502) to match requests for products and/or services form stakeholders (1504 . . . 1508) with products and/or service offerings from providers (1509 . . . 1513). These matches and any subsequent agreements may be recorded in one or more smart contracts which are recorded in one or more distributed ledger (1503). The marketplace (1501) may also provide matching services (1502) to the one or more providers (1509 . . . 1513) in any arrangement and can also match stakeholder service and/or product offerings (1509-1513) to the one or more providers (1509 . . . 1513). For example, if a stakeholder (e.g., 1507) is a carer, they may offer their services to, for example, a care facility (1510) through the marketplace and matching systems.

In some embodiments in addition to the unique identities established by the care village for stakeholders, there may also be memberships for various other organizations of these stakeholders. For example, a family may create a membership for the relatives of a PUM, where certain data is available to those members. This can include various classification or other organization schemata.

Such memberships can be represented by open or closed sets and may include organizational principles such as function, characteristics, capabilities, context, locations, temporal considerations and the like.

In some embodiments such marketplace may be linked, through for example at least one API to insurance providers, health care providers and/or other suppliers of products and services.

In some embodiments tokens may be form part of a set of forward-looking instruments, such that for example a token may be an option of a product, service, access to a stakeholder or other entity. For example, this may include the use of tokens as a means for forward and/or reserving booking, career's, equipment, facilities and the like. Such an approach may also be used for value-oriented transactions, such as the option to purchase insurance, health and wellness services, including procedure planning, medications and the specialists for such procedures and the like. This can include a secondary market for such tokens.

Example Embodiment:

A PERS (Personal Emergency Response System) device with multiple sensors, including, for example, accelerometer, altimeter, location (GPS, Wi-Fi and/or other), Bluetooth, and mobile networking capabilities can detect events and report them as tokens to other devices and/or to a server, for example a care hub. These tokens may contain the sensor data or may reference the data stored at the sensor. Those other devices in the monitoring environment and/or the server may make decisions on event response, for example escalation, without the need to access the information stored or referenced by the tokens. Other devices within the system may obtain the data that comprises and/or is bound to the token and use it to, for example, enhance the event detection accuracy and/or to confirm the event. For example, the PERS device may interpret a combination of acceleration and change in altitude from its sensors as a "fall" event (the PUM tripped and fell to the floor), issue a token associated with the sensors' data and send that event token to the server and to a nearby edge device. While the server may trigger a notification to a call center or to smart speaker app to initiate a conversation with the PUM, the nearby edge device may use the token, combined with its identification or other authorization key, to request the event data from the PERS device and use it to confirm and/or add accuracy to the fall event, by combining the PERS' sensor data with data from its own sensors, for example audio signals from a microphone or microphone array, or output signals from one or more FMCW radar sensors.

The PERS device may also issue tokens which can be combined with tokens or data from other devices to create proof of, for example a PUM-caregiver and/or other stakeholder interaction. For example, a caregiver may use a smartphone app to connect with the PERS device. This connection may use Bluetooth, which ensures that it only happens when the caregiver is in proximity to the PERS device and, therefore, to the PUM who carries it. Through the connection, the PERS device may transmit a token that uniquely identifies the device, and which may contain additional device and/or sensor data. This token can be used as proof that a scheduled visit to the PUM by the caregiver occurred at a specific time and location. The token may also be combined with tokens from other devices, for example, medical sensors or other medical equipment, to create proof that an expected/scheduled treatment or set of tests was performed on the PUM. The combination of tokens may happen within the devices, when the activities take place, or within a server or edge device, at a different location and time. In both cases the tokens that get combined and the resulting "proof token" can be stored in a DL and the process of verifying, combining and issuing proof can be performed by smart contracts, which helps improve privacy and reduce the risk of fraud.

In some embodiments, a token service provides token issuing, exchange and/or redemption capabilities to one or more system elements. These capabilities can include management and storage of such tokens, identity management systems for the tokens and one or more cryptographic services, including key management.

A token service may comprise any combination of these capabilities, for example a token service instantiated as part of a care hub may include these capabilities and further device specific functionality.

In some embodiments, an instance of a token service may issue tokens that have specific identifying characteristics, for example they comprise, at least in part, an identifier, such as a cryptographic reference in a specific range. For example, a computationally secure set of tokens may be used in an environment where access to that environment is restricted to specified authenticated sensors, devices and/or systems embedded within an environment. Where the token service is interacting across network connections that involve external to an environment connection, informationally secure cryptographic techniques may be employed.

A token service may be instantiated, in whole or in part, in a protected processing environment, for example as hardware using current off the shelf components, such as those available from Intel, ARM and AMD, as well as in proprietary hardware designs and those involving secure coprocessors, such as Apple units.

A token service may include one or more anti-tamper technologies, such as those that upon detecting tampering, such as side channel access attempts, will delete any secret keys held by such a device.

In some embodiments different types of tokens may be issued by a specialized token service, for example a data token may be issued by a token service that is part of a sensor, device and/or system, where that token service only has the capability to issue such data tokens and the token itself comprises identity of the sensor and encrypted data generated by the sensor. These are described herein as lightweight tokens.

A further example is the issuing by a token service of configuration tokens, where for example a sensor, device and/or system may issue one or more configuration tokens that are propagated to one or more other sensors, that upon receipt of such tokens, use the configuration data in the token to change their configuration. This can include one or more specifications as to the communication of data sets that are generated by the sensor after the received configuration is implemented by the sensor. For example, if the configuration specifies that a camera sensor is to record the images captured and store such images in a specified elastic repository, where these images may be used by a care processing system to evaluate whether a PUM has fallen or simply tripped. Whereas in normal operation such a camera would be configured to detect only edges of the images and compare those edges to the known horizontal and vertical surfaces of an environment so as to detect sudden changes in the orientation of the subject of the image capture, such as a PUM.

In some embodiments a token service may issue NFT's (Non-Fungible Tokens), which represent events and/or event sequences, which may involve multiple stakeholders over periods of time. For example, if a number of stakeholders are involved in a set of events, such as when a PUM transitions from one operating pattern to another, this change in behavior may be represented by an NFT. The NFT may include a data set that can be evaluated by one or more care processing systems, such that the data can be compared to transition patterns of other PUM with similar care and wellness conditions, without revealing any PII of the original PUM.

NFT's and other token types as representations of PUM data sets may when combined with one or more smart contracts support one or more ownership relationships of the data. For example, a PUM may select their data can be used for research, for example by an accredited university, however they may require that research, for example by a pharmaceutical company, be by request, to themselves or their proxy. This can, in some embodiments, lead to some form of value exchange between the PUM and the users of the data.

In some embodiments, this can include the use of distributed ledgers and smart contracts to, at least in part, provide support for any policies on the use of the data.

In another embodiment, a token service may have a limited set of tokens that can be issued, for example, over a period of time, in the presence of one or more stakeholder, at a specific location, by a specific sensor, device and/or system and the like.

In some embodiments, token services may be instantiated so as to provide token issuance and/or token redemption. This can include token services that are configured to redeem tokens, for example a token service embodied within a sensor or device, that can accept and interpret tokens from one or more authorized token issuing services. In some embodiments token services may comprise separate functional elements, for example token issuing, token evaluation, token redemption and the like.

In some embodiments tokens may provide an audit train for a set of activities, for example the undertaking of a service to a PUM, where the tokens generated as a part of that activity can provide a stakeholder with evidence of that activity, however the data form the activity may not be available to that stakeholder. For example, where an insurance company is the stakeholder.

In some embodiments, a token service may support the distribution of tokens to one or more digital twins, where such digital twin is cooperating with one or more care processing system so as to evaluate potential care and wellness situations for a PUM.

A care hub may form part of the monitoring systems for a PUM and their environment. The care hub can act as an intermediary between one or more sensors, devices and or systems such that the data generated by those sensors, devices and/or systems and other sensors, devices and/or systems to which that data can be communicated. In some environments this can include a care hub incorporating a token service that forms part of the management, communication and distribution of those data sets.

Such an embodiment may comprise one or more protected processing environments, such as Intel SGX, ARM Trustzone and the like, where the key generation, processing and/or storage may be instantiated. The use of hardware and hardware enabled token management systems can support both the integrity and security of the data. The token distribution specifications may include the specification of specific endpoints for the token, where those end points are uniquely configured for such token distribution. For example, an end point such as a device of stakeholder, for example a carer, may be configured to accept tokens only from specific care hubs and/or from specific sensors, devices and/or systems.

In some embodiments, a token created by a token service embedded in and configured by a care hub may include multiple data segments which are only available to specified stakeholders.

Figure 18:
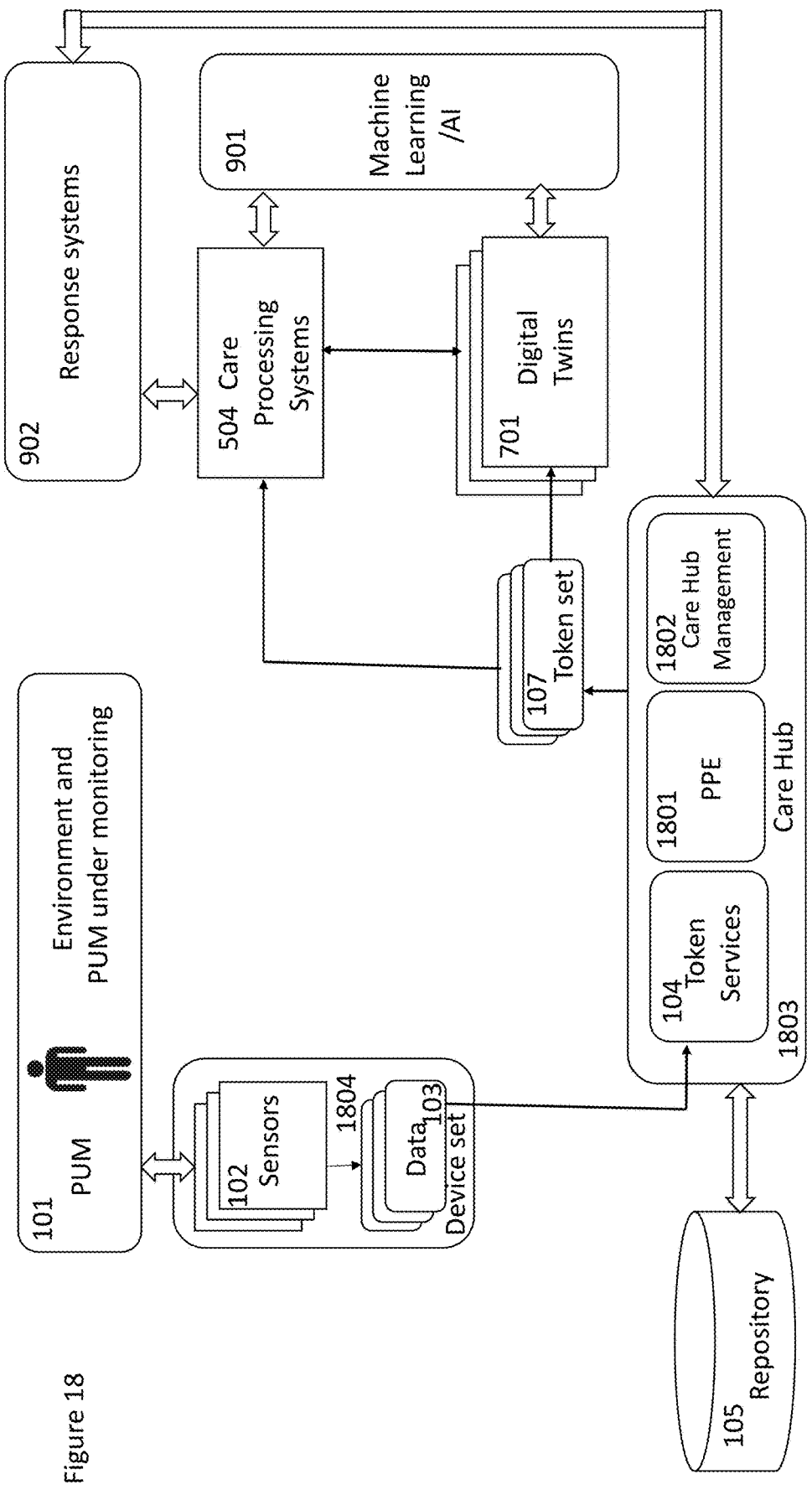
FIG. 18 illustrates a care hub.

FIG. 18 illustrates a care hub (1803), comprising, at least in part, one or more token services instance (104), a protected processing environment (1801) and a care hub management system (1802). In this example a set of devices (1804), comprising a set of sensors (102), generating data sets (103) securely communicates that data to a care hub (1803) configured to manage that data. The care hub (1803) using the PPE (1801) and the configuration and specifications managed by the care hub management systems (1802), creates and distributes sets of tokens (107) to other system elements, including care processing systems (504), digital twins (701) and response systems (902). The care processing (504) and digital twins (701) may invoke machine learning systems (901), where for example, data from machine learning systems (901) may also be communicated to care hub (1803), which in turn may include such data in, for example a multi-segment token as part of a token set (107). For example, this may be the case where a multi-dimensional feature set is used by machine learning (901) techniques to evaluate potential variations in the relationships of one or more dimensions, where such variations are expressed a in manner that can be used to configure one or more sensors, devices and/or systems to identify such a variation in their respective data sets.

Figure 19:
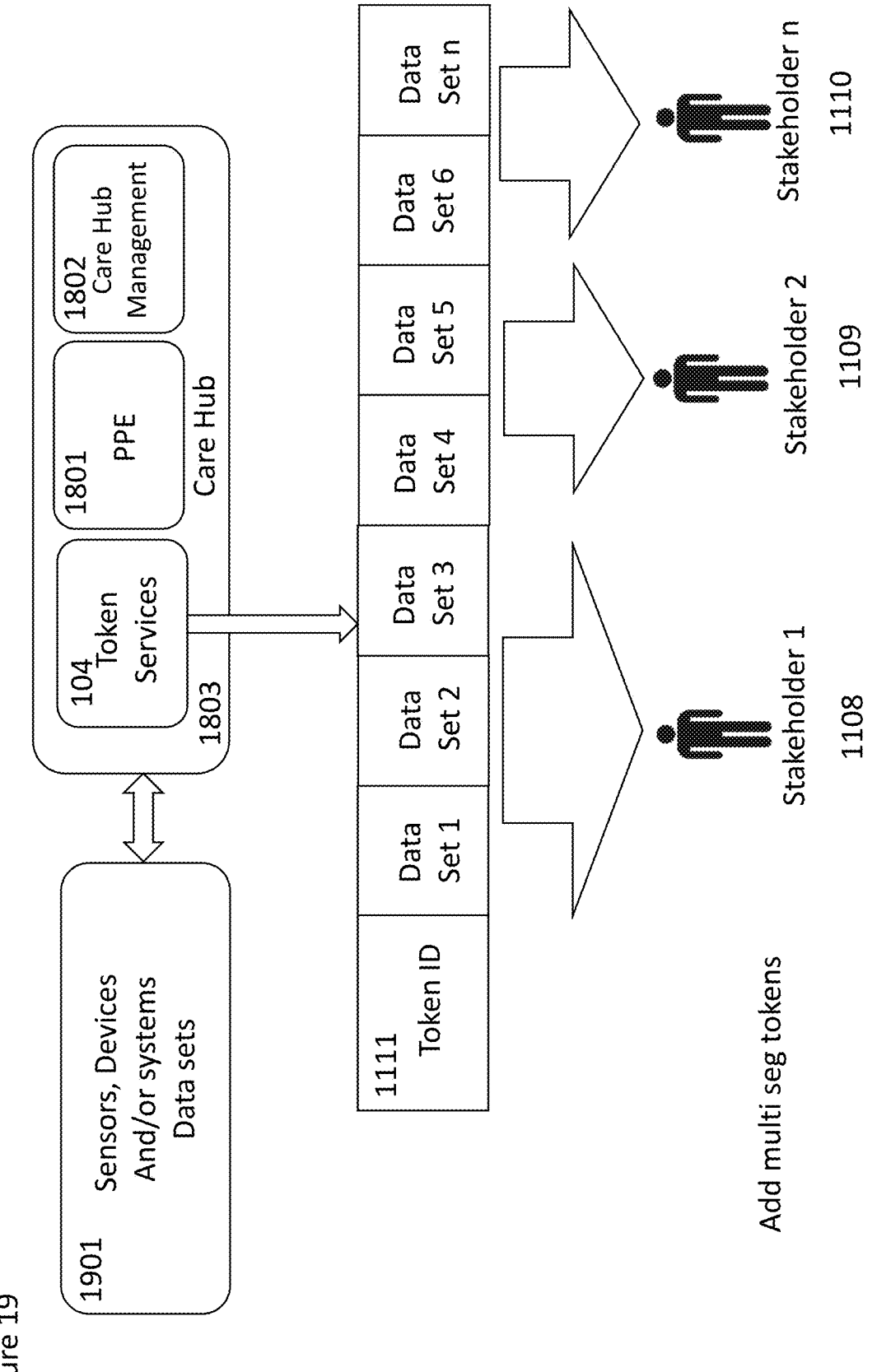
FIG. 19 illustrates a set of sensors, devices and/or systems generated data sets.

FIG. 19 illustrates a set of sensors, devices and/or systems generated data sets (1901), being processed by a care hub (1803) into a multi segment token (1111), where differing data sets are only available to different stakeholders (1108, 1109,1110). In some embodiments, devices representing such stakeholders may be configured to share such data in exigent circumstances, such as a medical emergency.

The previous description of the embodiments is provided to enable any person skilled in the art to practice the disclosure. Thus, the present disclosure is not intended to be limited to the embodiments shown herein but is to be accorded the widest scope consistent with the principles and features disclosed herein.

What is claimed is:

1. A care processing system to protect privacy of a person under care, the system comprising:

a transceiver configured to receive a detected data set that is detected by an environmental sensor deployed in an environment in which the environmental sensor monitors behaviors of the person under care that are related to a health, wellness or care condition of the person under care;

a non-transitory computer-readable storage medium storing:

a quiescent data set, the quiescent data set representing previous quiescent behaviors of the person under care in the environment, and at least one hardware processing unit configured to:

determine whether a health, wellness or care event for the person under care has occurred by comparing the detected data set against the quiescent data set, and in response to determining that the health, wellness or care event has occurred:

generate a token that includes a type indication for a type of the health, wellness or care event determined to have occurred and includes a data payload, wherein the type indication is encrypted via a first encryption key and the data payload is encrypted via a second encryption key, different from the first encryption key, wherein the second encryption key is selected based on the type of the health, wellness or care event determined to have occurred, and transmit, via the transceiver, the token to a stakeholder for care of the person under care.

2. The system of claim 1, wherein the first encryption key is selected based on at least one of the group consisting of:

the detected data set, an identity of the stakeholder, an identity of the person under care, an identity of the environmental sensor associated with the first token, a session of the person under care.

3. The system of claim 1, wherein the environmental sensor is a part of a plurality of environmental sensors, and the first data payload includes multiple detected data sets representing behaviors of the person under care in the environment from each environmental sensor of the plurality of environmental sensors.

4. The system of claim 1, wherein the second data payload is made available from the second token to the stakeholder based on a device associated with the stakeholder being determined to be within a specified proximity of the person under care.

5. The system of claim 1, wherein the transceiver is further configured to transmit the token to a second care token services module configured to decrypt the token.

6. The system of claim 5, wherein the second care system is determined based in part on the group of privacy conditions comprising:

the type of health, wellness or care event identified by the detected data set;

a relationship of the at least one stakeholder to the person under care;

a location in which the stakeholder is present; and whether a second stakeholder is present in the location with the stakeholder.

7. The system of claim 1, wherein the stakeholder to be notified of the health, wellness or care event being determined to have occurred is determined from among a plurality of stakeholders by data included in a health care profile (HCP) for the person under care that identifies that the health, wellness or care event is pertinent to the at least one stakeholder.

8. The system of claim 1, wherein the second encryption key is selected to make the data payload available to the stakeholder based on the stakeholder being determined to be engaged in a health, care, and wellness activity with the person under care.

9. The system of claim 1, wherein the second data payload is configured for storage constrained to a predefined time period after which the second data payload is erased.

10. The system of claim 1, wherein the second encryption key is selected to make the data payload available to the stakeholder in response to the type indication identifying an emergency event in the environment.

11. The system of claim 1, wherein the stakeholder is a first stakeholder, and wherein the at least one hardware processing unit is further configured, in response to determining that the health, wellness or care event has occurred, to:

transmit, via the transceiver, the token to a second stakeholder for care of the person under care, wherein both the first stakeholder and the second stakeholder have access to a decryption schema for the first encryption key, and wherein only one of the first stakeholder and the second stakeholder have access to a second decryption schema for the second encryption key.

12. The system of claim 1, wherein the stakeholder is a first stakeholder, and wherein the token includes a second payload, wherein the at least one hardware processing unit is further configured, in response to determining that the health, wellness or care event has occurred, to:

transmit, via the transceiver, the token to a second stakeholder for care of the person under care, wherein both of the first stakeholder and the second stakeholder have access to a decryption schema for the first encryption key, wherein only the first stakeholder of the first stakeholder and the second stakeholder has access to a first decryption schema for the data payload, wherein only the second stakeholder of the first stakeholder and the second stakeholder has access to a second decryption schema for the second payload.

13. The system of claim 1, wherein the non-transitory computer-readable storage medium further stores a health care profile (HCP) for the person under care that includes a privacy profile that identifies a set of conditions under which various data associated with the person under care are permitted to be accessible to parties identified in the privacy profile.

14. The system of claim 13, wherein the data payload is provided to the stakeholder in a preloaded format when current conditions at a time of transmission to the stakeholder do not satisfy the set of conditions under which the stakeholder is permitted access to the data payload.

15. The system of claim 1, wherein the stakeholder is one of a plurality of stakeholders for care of the person under care, wherein the at least one hardware processing unit is further configured, in response to determining that the health, wellness or care event has occurred, to:

control provision of a second decryption schema for the second encryption key among the plurality of stakeholders according to a privacy profile for the person under care.

16. The system of claim 15, wherein privacy profile specifies provision of the second decryption schema to decrypt and access contents of the data payload in response to the environmental sensor detecting a second event.

17. The system of claim 16, wherein the second event is selected from the group consisting of:

a presence of the stakeholder and the second person in an environment with the person under care;

a confirmation of an emergency from the person under care; and provision of a second token from a different care system from which the token was received.

18. The system of claim 1, wherein the data payload contains content selected from the group consisting of:

the detected data set;

a pointer to a storage location for the detected data set;

a multi-dimensional data set that combined the detected data set with a second detected data set; and an analysis of or determination based on the detected data set.

19. The system of claim 1, wherein the at least one hardware processing unit is further configured to:

identify pertinent data from a health care profile (HCP) for the person under care selected HCP with respect to the health, wellness or care event determined to have occurred, and include the pertinent data in the data payload.

20. A method by which privacy of a person under care is protected, comprising:

receiving a detected data set that is detected by an environmental sensor deployed in an environment in which the environmental sensor monitors behaviors of the person under care that are related to a health, wellness or care condition of the person under care;

comparing the detected data set against a quiescent data set, the quiescent data set representing previous quiescent behaviors of the person under care in the environment, to determine whether a health, wellness or care event has occurred in the environment;

in response to determining that the health, wellness or care event has occurred:

generating a token that includes a type indication for a type of the health, wellness or care event determined to have occurred and includes a data payload, including:

encrypting the type indication via a first encryption key;

selecting a second encryption key, different from the first encryption key, based on the type of the health, wellness or care event determined to have occurred; and encrypting the data payload via the second encryption key; and transmitting the token to a stakeholder for care of the person under care.

\* \* \* \* \*